US009199914B2

(12) United States Patent
Hediger

(10) Patent No.: US 9,199,914 B2
(45) Date of Patent: Dec. 1, 2015

(54) MULTIPLE SUBSTITUTED FLUOROMETHANES AS SELECTIVE AND BIOACTIVE ISOSTERES

(75) Inventor: Mark E. Hediger, Marlborough, MA (US)

(73) Assignee: MEH ASSOCIATES, INC., Marlborough, MA (US)

( * ) Notice: Subject to any disclaimer, the term of this patent is extended or adjusted under 35 U.S.C. 154(b) by 297 days.

(21) Appl. No.: 13/576,911

(22) PCT Filed: Feb. 3, 2011

(86) PCT No.: PCT/US2011/023657
§ 371 (c)(1),
(2), (4) Date: Aug. 2, 2012

(87) PCT Pub. No.: WO2011/097421
PCT Pub. Date: Aug. 11, 2011

(65) Prior Publication Data
US 2012/0302519 A1 Nov. 29, 2012

Related U.S. Application Data

(60) Provisional application No. 61/301,042, filed on Feb. 3, 2010.

(51) Int. Cl.
| *A61K 31/198* | (2006.01) |
| *A61K 31/145* | (2006.01) |
| *A61K 31/19* | (2006.01) |
| *A61K 31/44* | (2006.01) |
| *A61K 31/70* | (2006.01) |
| *A61P 31/04* | (2006.01) |
| *A61P 33/00* | (2006.01) |
| *C07C 229/20* | (2006.01) |
| *C07C 229/24* | (2006.01) |
| *C07H 5/10* | (2006.01) |
| *C07C 323/63* | (2006.01) |
| *C07C 229/12* | (2006.01) |
| *C07C 279/14* | (2006.01) |
| *C07C 323/27* | (2006.01) |
| *C07C 323/54* | (2006.01) |

(52) U.S. Cl.
CPC ............ *C07C 229/12* (2013.01); *C07C 229/24* (2013.01); *C07C 279/14* (2013.01); *C07C 323/27* (2013.01); *C07C 323/54* (2013.01); *C07C 323/63* (2013.01); *C07H 5/10* (2013.01)

(58) Field of Classification Search
CPC .. C07C 229/12; C07C 279/14; C07C 323/54; C07C 323/27; C07C 229/24; C07C 323/63; C07H 5/10
USPC ............ 514/47, 23, 350, 557, 561, 665; 536/122, 26.23; 546/298; 562/426, 562/557, 560, 571; 564/501; 435/15, 184
See application file for complete search history.

(56) References Cited

U.S. PATENT DOCUMENTS

| 4,873,221 A * | 10/1989 | Trainor .................. 514/21.9 |
| 5,917,074 A | 6/1999 | Hammond et al. |
| 7,592,446 B2 | 9/2009 | Huang |
| 2004/0033896 A1 | 2/2004 | Koether et al. |
| 2004/0138255 A1 * | 7/2004 | Huang et al. ........... 514/311 |
| 2005/0239774 A1 | 10/2005 | Ernst et al. |
| 2012/0302519 A1 | 11/2012 | Hediger |

FOREIGN PATENT DOCUMENTS

| JP | 2000-502687 A | 3/2000 |
| JP | 2003-508382 A | 3/2003 |
| WO | 2007077876 A1 | 7/2007 |
| WO | 2008094592 A1 | 8/2008 |
| WO | 2008141010 A2 | 11/2008 |

OTHER PUBLICATIONS

DesMarteau et al. Easy Preparation of Bioactive Peptides from the Novel N(I•Trinuoroethyl Amino Acids. Chem Lett pp. 1052-1053, 2000.*
Coster etal. Treatment of amoeboid herpetic ulcers with adenine arabinoside or trifiuorothymidine. Br J Ophthalmol 63:418-421, 1979.*
Weber et al. 2-(Tributylstannyl)-4-[3-(trifluoromethyl)-3H-diazirin-3-yllbenzyl Alcohol: A Building Block for Photolabeling and Cross-Linking Reagents of Very High Specific Radioactivity. J AM Chem Soc 117:3084-3095, 1995.*
Patani et al. Bioisosterism: A Rational Approach in Drug Design. Chem Rev 96:3147-3176, 1996.*
International Search Report and Written Opinion issued in PCT/US2011/023657 dated Jun. 3, 2011.
Dzeja and Terzic, Phosphotransfer networks and cellular energetics. J Exp Biol. Jun. 2003;206(Pt 12):2039-47.
Kihlberg et al., Synthesis of Strombine. A New Method for Monocarboxymethylation of Primary Amines. Acta Chemica Scandinavica B 1983;37:911-916.
Kukhar and Romanenko, Phosphorus and Fluorine—The Union for Bioregulators. Kern Ind. 2007;56(6):329-344.
Yoo and Houk, Theory of Substituent Effects on Pericyclic Reaction Rates: Alkoxy Substituents in the Claisen Rearrangement. J Amer Chem Soc. 1997;119(12):2877-2884.
Office Action issued by the JPO in related application No. 2012-552093 dated Jan. 28, 2015—incl Engl lang trans).
Capone et al., Electrophilic S-Trifluoromethylation of Cysteine Side Chains in α- and β-Peptides: Isolation of Trifluoro-methylated Sandostatin® (Octreotide) Derivatives. Helvetica Chimia Acta, 2008;91(11):2035-2056.

(Continued)

*Primary Examiner* — Mark Shibuya
*Assistant Examiner* — Yih-Horng Shiao
(74) *Attorney, Agent, or Firm* — Sam K. Tahmassebi

(57) ABSTRACT

Disclosed herein are substituted fluoromethanes; pharmaceutical compositions comprising a therapeutically effective amount of the same; processes for preparing these fluoromethanes; and methods of using the same in alleviating infection and parasitism. Also disclosed are methods for identifying substituted fluoromethanes for modulating the activity of receptors and enzymes that bind and/or modify phosphate containing ligands and substrates.

9 Claims, 1 Drawing Sheet

(56) References Cited

OTHER PUBLICATIONS

Coombs and Mottram, Trifluoromethionine, a Prodrug Designed against Methionine γ-Lyase-Containing Pathogens, Has Efficacy In Vitro and In Vivo against Trichomonas vaginalis. Antimicrob Agents Chemother. Jun. 2001;45(6):1743-1745.

Kieltsch et al., Mild Electrophilic Trifluoromethylation of Carbon- and Sulfur-Centered Nucleophiles by a Hypervalent Iodine(III)—CF3 Reagent. Angew Chem Int Ed Engl. 2007;46(5):754-757.

Kolycheva et al., Fluorine-containing amino acids. VII. Polyfluoroalkoxy and polyfluoromethylthio derivatives of phenylalanine. J Organic Chem (Russian), Jun. 1989;25(6):1306-1311.

Langlois et al., Synthesis of S-trifluoromethyl-containing alpha-amino acids from sodium trifluoromethanesulfinate and dithio-amino acids, J Fluorine Chem. 1994;68(1):63-66.

Yoshimura et al., L-Methionine-gamma-lyase as a Target to Inhibit Malodorous Bacterial Growth by Trifluoromethionine, Biochem Biophys Res Commun. Apr. 12, 2002;292(4):964-968.

* cited by examiner

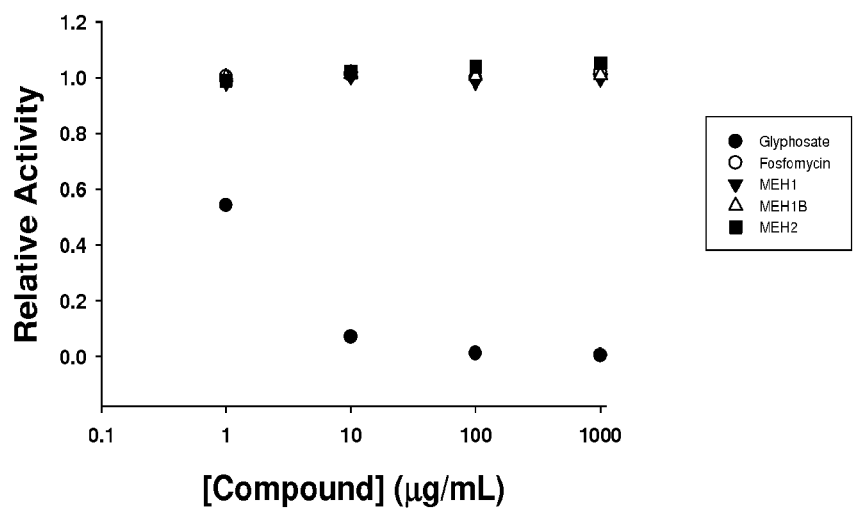
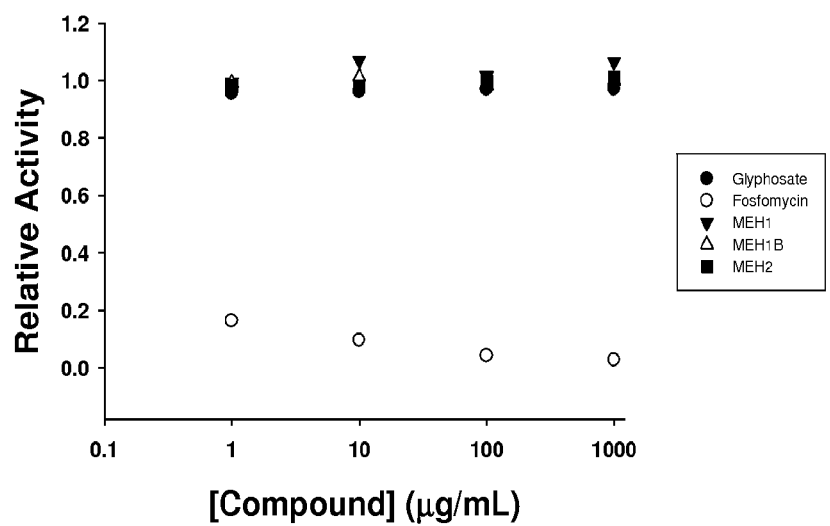

MULTIPLE SUBSTITUTED FLUOROMETHANES AS SELECTIVE AND BIOACTIVE ISOSTERES

RELATED APPLICATIONS

The present application is filed under 35 U.S.C. §371 as the U.S. national phase of International Application PCT/US2011/023657 filed Feb. 3, 2011, which designated the U.S. and claims priority to the U.S. Provisional Application Ser. No. 61/301,042, filed on Feb. 3, 2010, by Mark E. Hediger, and entitled "MULTIPLE SUBSTITUTED FLUOROMETHANES AS SELECTIVE AND BIOACTIVE ISOSTERES", the entire disclosure of both of which, including the drawings, is hereby incorporated by reference herein.

FIELD OF THE INVENTION

The disclosure herein relates to substituted trifluoromethanes and difluoromethanes that are useful mimics of biological phosphate. The disclosure further relates to compositions containing the substituted fluoromethane functionality and the processes of preparing and methods of identifying and utilizing such compounds.

BACKGROUND OF THE DISCLOSURE

Biological phosphate fulfills a central role in energy-transduction manifolds as well as biosynthetic and cellular signaling pathways in both prokaryotic and eukaryotic organisms. In spite of this fundamental role for phosphorylated biomolecules in cellular processes, significant limitations are encountered by those studying these pathways due to the unique charged nature of both the intermediates and the mimics historically employed as molecular probes of these processes (Knowles, J. R. Ada Doisy Lecture, University of Illinois at Urbana-Champaign, 1985). The paradox surrounding phosphate remains: The unique anionic character of biological phosphate and the controlled lability of this functional group remain the crux of cellular energetics and regulation; nonetheless, these very molecular properties are the essence of the challenges faced by those seeking to understand a multitude of cellular processes at the molecular level as well as those endeavoring to impact clinical outcomes. Through integrated design considerations disclosed herein, these mechanistic chemistries, biophysical properties and mimicries of biological phosphorylation may serve as the three-fold basis of a fundamental approach towards small molecule interrogations of these biological processes and the resultant medical interventions.

A novel, specific and physiologically stable mimic of this key biological switch would greatly enhance multiple approaches towards a more complete understanding of cellular processes surrounding phosphorylated intermediates and compounds. Such a specific biological probe would serve as a powerful research tool at the molecular level and as a potential gateway entry into the fields of diagnostic reporters and pharmaceuticals at the level of the entire organism. Multiple techniques for evaluation of such an appropriate probe would be enhanced by the unique atomic characteristics of a well-designed and specific mimic. Increased bioavailabilities may directly correspond with enhanced sensitivities in diagnostic settings, while higher potencies and greater selectivities at specific targets and receptors may be realized in clinical pharmaceutical applications.

The transient, selective and site-specific covalent attachment of a phosphate group to various biological molecules is one of the most (if not the) fundamental mechanisms of cellular regulation at the molecular level (Dzeja, P. P. and Terzic, A. J Exp Bio 206: 2039 (2003)). The potential of this isosteric replacement to positively impact clinical outcomes in the context of cell signaling processes, energetic transformations, ion channel regulation, cell cycle regulation, lipid metabolism, saccharide metabolism and processing, cytoskeletal regulation, DNA and RNA analoging as well as nearly all other biologically relevant phosphate binding events is a fundamental extension of the isostere's molecular design. Furthermore, impact upon the structural role phosphorous plays in bone and tooth development, metabolism and degradation processes is a further contemplated application of the disclosure.

SUMMARY OF THE INVENTION

Disclosed herein are substituted fluoromethanes; pharmaceutical compositions comprising a therapeutically effective amount of the same; processes for preparing these fluoromethanes; and methods of using the same in alleviating infection and parasitism. Also disclosed are methods for identifying substituted fluoromethanes for modulating the activity of receptors and enzymes that bind and/or modify phosphate containing ligands and substrates.

BRIEF DESCRIPTION OF THE DRAWINGS

FIG. 1 is bar graphs showing the enzymatic activity of some of the compounds disclosed herein as expressed in percentage of the respective control (minus inhibitor).

DETAILED DESCRIPTION OF THE EMBODIMENTS

In one aspect disclosed herein are substituted trifluoromethanes of formula I:

(I)

wherein,

A is independently selected from one or more functionalities selected from the group consisting of (a) amino acids, (b) carbohydrates, (c) lipids and lipid derivatives, (d) metabolic intermediates, (e) cofactors and (f) sub-molecular compositions shown to be biologically active.

The term "amino acids" includes, but is not limited to, peptides, hormones and proteins, while the term "carbohydrates" includes, but is not limited to, sugars, oligosaccharides, and polysaccharides. Furthermore, combinations of the above functionalities, such as a glycosylated peptide or a glycosylated hormone or a glycosylated protein, elaborated with the disclosed mimic are understood as members of the contemplated set A as illustrated by (I).

Other classes of compounds commonly known as inositols, prenylation intermediates, eicosanoid precursors and monomeric and polymeric nucleotides are further understood and contemplated within the context of the present disclosure.

In one embodiment are compounds of formula Ia:

(Ia)

where

A is as defined above;

X is selected from the group consisting of (a) oxygen, (b) sulfur (c) carbon, (d) silicon, (e) selenium and (f) any non-hydrogen atom or atomic null capable of serving as a covalent link between functionality A and the carbon of the parent trifluoromethane such that chemical stability of the compound is achieved and all valance requirements of linker X are satisfied. Furthermore, the linker, X, may consist of a series of atoms (2-12) allowing the optimal positioning of the trifluoromethyl functionality relative to the atomic sets defined as A within a given macromolecular binding site.

In some embodiments, X is an oxygen atom.

In some embodiments, X is a sulfur atom, S(O), or $SO_2$.

In some embodiments, X is $CR_1R_2$ or $SiR_1R_2$, where $R_1$ and $R_2$ are each independently selected from the group consisting of hydrogen, alkyl, aryl, heteroaryl, halogen, hydroxyl, thiol, amino, ether, thioether, alkyl amine, dialkyl amine, aryl amine, diaryl amine, and alkyl aryl amine. In some embodiments where X is $CR_1R_2$, $R_1$ and $R_2$ taken together form a cabonyl (=O), thiocarbonyl (=S) or substituted alkenyl (=C).

In some embodiments, X is a selenium atom or Se(O).

In some embodiments, X is $NR_3$, where $R_3$ is selected from the group consisting of hydrogen, alkyl, aryl, heteroaryl, heteroalicyclyl, hydroxyl, thiol, amino, ether, thioether, alkyl amine, dialkyl amine, aryl amine, diaryl amine, and alkyl aryl amine.

In some embodiments, X is a substituted or unsubstituted linker, 2-12 atoms in length, including substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, substituted or unsubstituted heteroalicyclyl or substituted or unsubstituted ether, substituted or unsubstituted thioether, and substituted or unsubstituted amine.

In another embodiment of the disclosure are compounds of formula Ib:

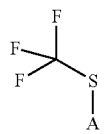

(Ib)

where A is as defined above and S is a sulfur atom.

In some embodiments, A in the compounds of formula I is an amino acid selected from the group consisting of tyrosine, serine, and threonine, or other amino acid residues without limitation. Certain embodiments of these compounds are compounds of formula Ic, Id, or Ie:

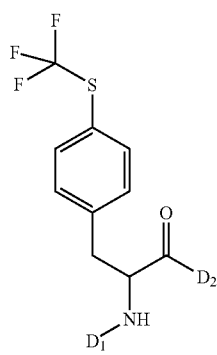

(Ic)

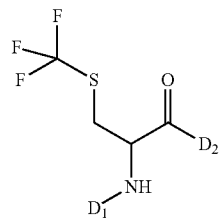

(Id)

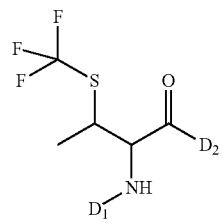

(Ie)

where $D_1$ and $D_2$ is each independently selected from the group consisting of hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, substituted or unsubstituted heteroalicyclyl, substituted or unsubstituted ether, substituted or unsubstituted thioether, and substituted or unsubstituted amine, or other independent amino acids or a sequence of one to one thousand (1-1000) of such amino acids. In the context of the independent amino acid sequences defined above, the common definitions of peptide and protein are understood as well as non-natural and β-amino acids and higher homologues without limitation.

In some embodiments, disclosed herein are analogues of compounds Ic-Ie, where the phenyl ring is replaced with other aromatics, such as naphthalene, biphenyl, or heteroaromatics, such as pyridine, thiophene, furan and imidazole and substituted analogues of these heteroaromatics such as ortho-pyridones (2-hydroxy pyridines), 2-phenyl thiophenes, 3-pyrazole furans, 2-hydroxy-4-methyl imidazoles or other substituted heteroaromatics. Furthermore, analogues of compounds (Ic-Ie) corresponding to positional or stereochemical isomers such as meta-hydroxy phenylalanine or D-tyrosine or modified amino acids understood as rigidified or conformationally restrained or metabolically stabilized analogues such as hydroxylproline or homo-serine or N-methyl L-tyrosine are further contemplated without limitation in this disclosure. It is further understood that a glycosylated peptide or hormone or protein functionalized at an amino acid residue with the parent trifluoromethane group is contemplated in the context of the present aspect of this disclosure.

In some embodiments, A in the compounds of formula I is glucose or fructose. In some of these embodiments, disclosed herein are compounds of formula If or Ig:

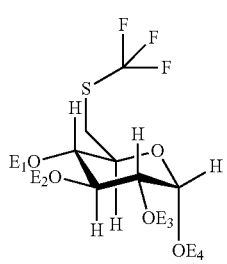

(If)

(Ig)

where
E₁-E₄ is each independently selected from the group consisting of hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, substituted or unsubstituted heteroalicyclyl, substituted or unsubstituted ether, substituted or unsubstituted thioether, and substituted or unsubstituted amine or single carbohydrates or an ensemble of carbohydrates containing one to one thousand (1-1000) members.

In the context of the independent carbohydrate sequences defined above, the common definitions of carbohydrate and polysaccharide are understood. Furthermore, in some embodiments, disclosed herein are analogues of compounds (If-Ig) corresponding to positional or stereochemical isomers such as L-glucose or D-mannose or α-lactose or sucrose or modified carbohydrates, as rigidified or conformationally restrained, or metabolically stabilized analogues such as sialic acid or shikimic acid or myo-inositol or steviol. In other embodiments, A is a peptide or protein or lipid covalently modified with a carbohydrate or polysaccharide wherein that carbohydrate or polysaccharide is further functionalized by the parent trifluoromethane group.

In another embodiment, A in the compounds of formula I, is a substituted analogue of sphingosine. In some of these embodiments, disclosed herein are compounds of formula (Ih):

(Ih)

where
G1-G4 is each independently selected from the group consisting of hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, substituted or unsubstituted heteroalicyclyl, substituted or unsubstituted ether, substituted or unsubstituted thioether, and substituted or unsubstituted amine or single carbohydrates or a ensemble of carbohydrates containing one to one thousand (1-1000) members.

In some embodiments, the sphingosines is selected from the group consisting of ceramide, sphingomyelins, and glycososphingolipids. In further embodiments, the sphingosines is selected from the group consisting of cereborsides and gangliosides. Analogues of compounds (Ih) corresponding to positional or stereochemical isomers are understood as are rigidified or conformationally restrained or metabolically stabilized analogues without limitation in this disclosure.

In some embodiments, A in the compounds of formula I is enol pyruvate or creatine. In some of the embodiments, disclosed herein are compounds of formula Ii or Ij:

(Ii)

(Ij)

In some embodiments, A in the compounds of formula I is adenosine diphosphate or pyridoxal or other cofactors. In some of the embodiments, disclosed herein are compounds of formula Ik or Il:

(Ik)

(Il)

In some embodiments, A in the compounds of formula I is des-phosphonate glyphosate or des-phosphonate homo-glyphosate or other glyphosate analogues. In some of the embodiments, disclosed herein are compounds of formula (Im):

(Im)

In another aspect disclosed herein there are substituted difluoromethanes of formula II:

where

A and B are each independently selected from (a) desphosphate nucleic acids or (b) biologically active substituents. Iterative covalent bonding and linear polymerization of these difluoromethanes are contemplated herein.

In one embodiment are compounds of formula (IIa):

where

X and Y is each independently selected from the group consisting of (a) oxygen, (b) sulfur (c) carbon, (d) silicon, (e) selenium and (f) any non-hydrogen atom or atomic null capable of serving as a covalent link between functionality A or B and the carbon of the parent difluoromethane such that chemical stability of the compound is achieved and all valance requirements of linkers X and Y are satisfied. Furthermore, the linker, X, may consist of a series of atoms (2-12) allowing the optimal positioning of the difluoromethyl functionality relative to substituent A within a given macromolecular binding site.

In some embodiments, X and Y is each independently oxygen.

In some embodiments, X and Y is each independently sulfur, S(O), or $SO_2$.

In some embodiments, X and Y is each independently $CR_1R_2$ or $SiR_1R_2$, where $R_1$ and $R_2$ is each independently selected from the group consisting of hydrogen, alkyl, aryl, heteroaryl, halogen, hydroxyl, thiol, amino, ether, thioether, alkyl amine, dialkyl amine, aryl amine, diaryl amine, alkyl aryl, and amine. In some embodiments where X is $CR_1R_2$, $R_1$ and $R_2$ taken together form a cabonyl (=O), thiocarbonyl (=S) or substituted alkenyl (=C).

In some embodiments, X and Y is each independently selenium or Se(O).

In some embodiments, X and Y is each independently $NR_3$, where $R_3$ is selected from the group consisting of hydrogen, alkyl, aryl, heteroaryl, hydroxyl, thiol, amino, ether, thioether, alkyl amine, dialkyl amine, aryl amine, diaryl amine, and alkyl aryl amine.

In some embodiments, X and Y is each independently a substituted or unsubstituted linker, 2-12 atoms in length, selected from the group consisting of substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, substituted or unsubstituted heteroalicyclyl, substituted or unsubstituted ether, substituted or unsubstituted thioether, and substituted or unsubstituted amine.

In some embodiments, X and Y is each independently a methylene group.

In another embodiment of the disclosure are compounds of formula IIb or IIc:

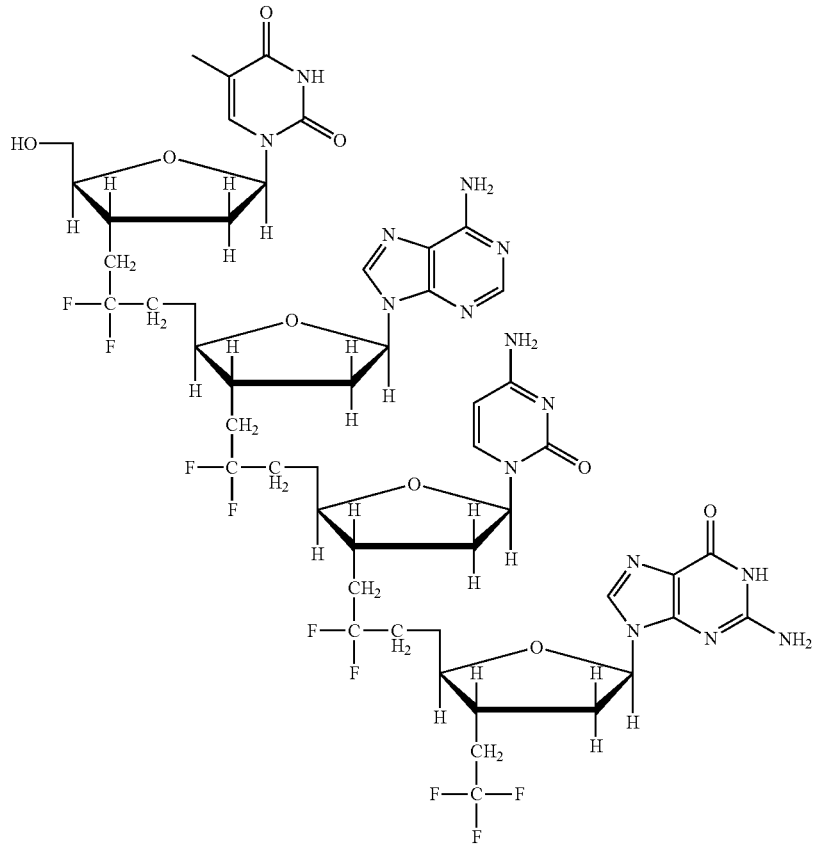

(IIc)

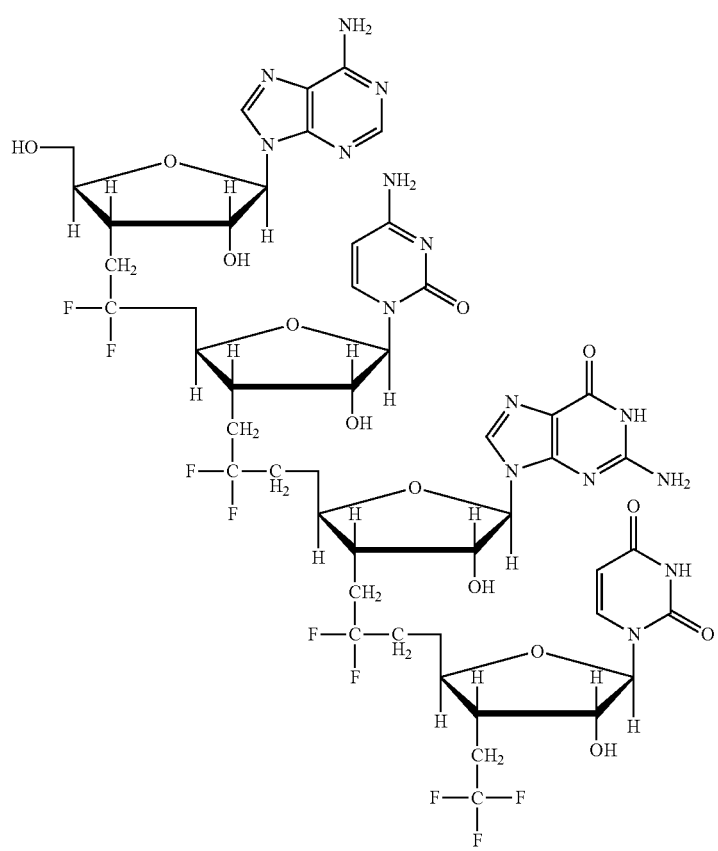

Iterative covalent bonding and linear polymerization (n=1 to n=5000) of these substituted difluoromethanes is presently contemplated herein. For example, the compound of formula IIb or IIc is the compound where n=4. The monomeric nucleotide units may carry the purine and pyrimidine bases corresponding to adenine, guanine, cytosine and thymine as well as other functionally stable bases. The terminal 3'-end of the compound may be substituted with the trifluoromethyl group as disclosed for the compound of formula I.

II. Pharmaceutical Preparations

In another aspect, disclosed herein is a pharmaceutical composition comprising a therapeutically effective amount of a compound of any one of Formula I or II and a pharmaceutically acceptable carrier, excipient, or diluent.

As used herein, a "therapeutically effective amount" refers to an amount of a compound that elicits the desired biological or medicinal response in a subject.

As used herein, a "pharmaceutical composition" refers to a mixture of a compound of this invention with other chemical components such as diluents, carriers or other excipients. A pharmaceutical composition may facilitate administration of the compound to a subject. Many techniques of administering a compound exist are known in the art, such as, without limitation, orally, intramuscularly, intraocularly, intranasally, parenterally, intravenously and topically. Pharmaceutical compositions will generally be tailored to the specific intended route of administration.

As used herein, a "carrier" refers to a compound that facilitates the incorporation of a compound into cells or tissues. For example, without limitation, dimethyl sulfoxide (DMSO) is a commonly utilized carrier that facilitates the uptake of many organic compounds into cells or tissues of a subject.

As used herein, a "diluent" refers to an ingredient in a pharmaceutical composition that lacks pharmacological activity but may be pharmaceutically necessary or desirable. For example, a diluent may be used to increase the bulk of a potent drug whose mass is too small for manufacture or administration. It may also be a liquid for the dissolution of a drug to be administered by injection, ingestion or inhalation. A common form of diluent in the art is a buffered aqueous solution such as, without limitation, phosphate buffered saline that mimics the composition of human blood.

The compounds of this invention can be administered to a subject per se, or in a pharmaceutical composition where they are mixed with other active ingredients as, for example, in a combination therapy, or suitable carriers or excipient(s). Techniques for formulation and administration of the compounds of the instant application may be found in "Remington's Pharmaceutical Sciences," Mack Publishing Co., Easton, Pa., 18th edition, 1990.

Suitable routes of administration may, without limitation, include oral, rectal, transmucosal, or intestinal administration; parenteral delivery, including intramuscular, subcutaneous, intravenous, intramedullary injections, as well as intrathecal, direct intraventricular, intraperitoneal, intranasal, intraocular injections or as an aerosol inhalant.

Alternatively, one may administer the compound in a local rather than systemic manner, for example, via injection of the compound directly into the area of pain or inflammation, often in a depot or sustained release formulation. Furthermore, one may administer the drug in a targeted drug delivery system, for example, in a liposome coated with a tissue-specific antibody. The liposomes will be targeted to and taken up selectively by the organ.

The pharmaceutical compositions disclosed herein may be manufactured procedures well-known in the art, e.g., by means of conventional mixing, dissolving, granulating, dragee-making, levigating, emulsifying, encapsulating, entrapping or tabletting processes.

Pharmaceutical compositions for use in accordance with the present disclosure thus may be formulated in conventional manner using one or more pharmaceutically acceptable carriers comprising excipients and auxiliaries, which facilitate processing of the active compounds into preparations, which can be used pharmaceutically. Proper formulation is dependent upon the route of administration chosen. Any of the well-known techniques, carriers, and excipients may be used as suitable and as understood in the art; e.g., in Remington's Pharmaceutical Sciences, above.

For injection, the agents disclosed herein may be formulated in aqueous solutions, preferably in physiologically compatible buffers such as Hank's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds disclosed herein to be formulated as tablets, pills, dragees, capsules, liquids, gels, syrups, slurries, suspensions and the like, for oral ingestion by a patient to be treated. Pharmaceutical preparations for oral use can be obtained by mixing one or more solid excipient with pharmaceutical combination disclosed herein, optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations, which can be used orally, include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present disclosure are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances, which increase the viscosity of the suspension, such as sodium carboxymethyl cellulose, sorbitol, or dextran. Optionally, the suspension may also contain suitable stabilizers or agents, which increase the solubility of the compounds to allow for the preparation of highly, concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

A pharmaceutical carrier for the hydrophobic compounds disclosed herein is a co-solvent system comprising benzyl alcohol, a nonpolar surfactant, a water-miscible organic polymer, and an aqueous phase. A common co-solvent system used is the VPD co-solvent system, which is a solution of 3% w/v benzyl alcohol, 8% w/v of the nonpolar surfactant Polysorbate 80™, and 65% w/v polyethylene glycol 300, made up to volume in absolute ethanol. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may be used.

Alternatively, other delivery systems for hydrophobic pharmaceutical compounds may be employed. Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semi-permeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

Many of the compounds used in the pharmaceutical combinations disclosed herein may be provided as salts with pharmaceutically compatible counterions. Pharmaceutically compatible salts may be formed with many acids, including but not limited to hydrochloric, sulfuric, acetic, lactic, tartaric, malic, succinic, etc. Salts tend to be more soluble in aqueous or other protonic solvents than are the corresponding free acids or base forms.

Pharmaceutical compositions suitable for use in the methods disclosed herein include compositions where the active ingredients are contained in an amount effective to achieve its intended purpose. More specifically, a therapeutically effective amount means an amount of compound effective to prevent, alleviate or ameliorate symptoms of disease or prolong the survival of the subject being treated. Determination of a therapeutically effective amount is well within the capability of those skilled in the art, especially in light of the detailed disclosure provided herein.

The exact formulation, route of administration and dosage for the pharmaceutical compositions disclosed herein can be chosen by the individual physician in view of the patient's condition. (See e.g., Fingl et al. 1975, in "The Pharmacological Basis of Therapeutics", Ch. 1 p. 1). Typically, the dose range of the composition administered to the patient can be from about 0.5 to 1000 mg/kg of the patient's body weight, or 1 to 500 mg/kg, or 10 to 500 mg/kg, or 50 to 100 mg/kg of the patient's body weight. The dosage may be a single one or a series of two or more given in the course of one or more days, as is needed by the patient. Note that for almost all of the specific compounds mentioned in the present disclosure, human dosages for treatment of at least some condition have been established. Thus, in most instances, the methods disclosed herein will use those same dosages, or dosages that are between about 0.1% and 500%, or between about 25% and 250%, or between 50% and 100% of the established human dosage. Where no human dosage is established, as will be the case for newly-discovered pharmaceutical compounds, a suitable human dosage can be inferred from $ED_{50}$ or $ID_{50}$ values, or other appropriate values derived from in vitro or in vivo studies, as qualified by toxicity studies and efficacy studies in animals.

Although the exact dosage will be determined on a drug-by-drug basis, in most cases, some generalizations regarding the dosage can be made. The daily dosage regimen for an adult human patient may be, for example, an oral dose of between 0.1 mg and 500 mg of each ingredient, preferably between 1 mg and 250 mg, e.g. 5 to 200 mg or an intravenous, subcutaneous, or intramuscular dose of each ingredient between 0.01 mg and 100 mg, preferably between 0.1 mg and 60 mg, e.g. 1 to 40 mg of each ingredient of the pharmaceutical compositions disclosed herein or a pharmaceutically acceptable salt thereof calculated as the free base, the composition being administered 1 to 4 times per day. Alternatively the compositions disclosed herein may be administered by continuous intravenous infusion, preferably at a dose of each ingredient up to 400 mg per day. Thus, the total daily dosage by oral administration of each ingredient will typically be in the range 1 to 2000 mg and the total daily dosage by parenteral administration will typically be in the range 0.1 to 400 mg. Suitably the compounds will be administered for a period of continuous therapy, for example for a week or more, or for months or years.

Dosage amount and interval may be adjusted individually to provide plasma levels of the active moiety, which are sufficient to maintain the modulating effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations.

Dosage intervals can also be determined using MEC value. Compositions should be administered using a regimen, which maintains plasma levels above the MEC for 10-90% of the time, preferably between 30-90% and most preferably between 50-90%.

In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

The compositions may, if desired, be presented in a pack or dispenser device, which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions comprising a compound disclosed herein formulated in a compatible pharmaceutical carrier may also be prepared, placed in an appropriate container, and labeled for treatment of an indicated condition.

III. Activity of the Compounds

In another aspect, disclosed herein is a method of modulating the activity of a phosphoenolpyruvyl transferase (PEPT) enzyme, comprising: contacting the PEPT enzyme with a compound of any one of Formulae I or II as described herein. In some embodiments, the method further comprises the step of detecting a change in the activity of the enzyme, and/or comparing the activity of the enzyme after the contacting to the activity of the enzyme before the contacting. In some embodiments, the compound of any one of Formulae I or II is a competitive inhibitor of the PEPT enzymes. In other embodiments, the compound of any one of Formulae I or II is an un-competitive inhibitor of the PEPT enzymes. In yet other embodiments, the compound of any one of Formula I or II is a non-competitive inhibitor of the PEPT enzymes. In still other embodiments, the compound of any one of Formulae I or II is a mixed inhibitor of the PEPT enzymes.

As used herein, to "modulate" the activity of an PEPT enzyme means either to activate it, i.e., to increase its cellular function over the base level measured in the particular environment in which it is found, or deactivate it, i.e., decrease its cellular function to less than the measured base level in the environment in which it is found and/or render it unable to perform its cellular function at all even in the presence of a natural binding partner. A natural substrate partner is an endogenous molecule that is a substrate for the enzyme.

As used herein, to "detect" changes in the activity of a PEPT enzyme refers to the process of analyzing the result of an experiment using whatever analytical techniques are best suited to the particular situation. In some cases simple visual observation may suffice, in other cases the use of a microscope, visual or UV light analyzer or specific bioassays may be required. The proper selection of analytical tools and techniques to detect changes in the activity of PEPT enzymes are well-known and will be apparent to those skilled in the art based on the disclosures herein.

As used herein, a "competitive inhibitor" refers to a compound that binds to an enzyme in preference over a substrate to form an enzyme-inhibitor complex that modulates the pharmacological response associated with that particular enzyme.

As used herein, "uncompetetive inhibitor" refers to a compound that has an affinity for an enzyme-substrate complex to form an enzyme-substrate-inhibitor complex that modulates the pharmacological response associated with that particular enzyme.

As used herein, "non-competetive inhibitor" refers to a compound that reduces the maximum rate of an ezymatic reaction without changing the apparent binding affinity of the substrate thus modulating the pharmacological response associated with that particular enzyme.

As used herein, "mixed inhibitor" refers to a compound that binds to an enzyme or enzyme-substrate complex that changes both the affinity of the enzyme for the substrate and reduces the maximal rate of an enzymatic reaction thus modulating the pharmacological response associated with that particular enzyme.

In some embodiments, the above enzyme is contacted with the compound of any one of Formula I or II in vivo, e.g., when the enzyme is in a tissue or in an animal. In other embodiments, the above enzyme is contacted with the compound of any one of Formula I or II in vitro, e.g., in an assay, or when the enzyme is in an intact cell or in a plurality of cells.

In some embodiments, the compound of any one of Formulae I or II selectively modulates the PEPT enzyme activity relative to other enzymes that utilize phosphoenolpyruvate as a substrate. In some embodiments, the other enzymes that utilize phosphoenolpyruvate comprise the Krebs cycle enzymes.

Throughout the present disclosure, the PEPT enzyme can be selected from the group consisting of a bacterial PEPT enzyme, a fungal PEPT enzyme, a plant PEPT enzyme, a trypanosomal PEPT enzyme, a protozoan PEPT enzyme or any other non-mammalian organism expressing the PEPT enzyme.

In another aspect, disclosed herein is a method of alleviating bacterial, fungal or trypanosomal infection or parasitism in a subject, comprising: identifying a subject in need thereof; and administering to the subject a therapeutically effective amount of a compound of any one of Formulae I or II. In some embodiments, the subject is a patient.

As used herein, a "subject" refers to an animal that is the object of treatment, observation or experiment. "Animal" includes cold- and warm-blooded vertebrates and invertebrates such as fish, shellfish, reptiles and, in particular, mammals. "Mammal" includes, without limitation, mice; rats; rabbits; guinea pigs; dogs; cats; sheep; goats; cows; horses; primates, such as monkeys, chimpanzees, and apes; and, in particular, humans.

As used herein, a "patient" refers to a subject that is being treated by a medical professional such as an M.D. or a D.V.M. to attempt to cure, or at least ameliorate the effects of, a particular disease or disorder or to prevent the disease or disorder from occurring in the first place.

In some embodiments, the infection or parasitism is caused by vectored diseases such as malaria, Chagas disease, sleeping sickness, leishmaniasis or Lyme disease or is as an unintended consequence of medical therapies including, but not limited to, invasive surgeries, antibiotic treatments or antiviral treatments.

In another aspect, disclosed herein is a method of identifying a compound that modulates the activity of a PEPT enzyme, comprising: contacting the PEPT enzyme with a plurality of compounds of any one of Formulae I or II one at a time; comparing the activity of the enzyme after the contacting with each compound of any one of Formulae I or II to the activity of the enzyme before the contacting; and selecting a compound of any one of Formulae I or II that changes the activity of the enzyme after the contacting.

In some embodiments, the enzyme is located within a cell, while in other embodiments, the enzyme is located within a plurality of cells. In further embodiments, the enzyme is located within a cell extract that expresses the enzyme, e.g., a cell extract that contains the genetic code for any of the PEPT enzymes.

Contacting a cell or plurality of cells may comprise incubating the cell(s) with the test compound. The cell(s) may be engineered to over-express the enzyme. The assay may further comprise the addition of a known inhibitor to the test milieu to assist in differentiating a competetive inhibitor from a non-competetive inhibitor. In general, if the basal activity of the enzyme, as measured before any compound is added, is decreased, the compound is likely an inhibitor.

In another aspect, disclosed herein is a method of identifying a compound effective for the treatment of infection and non-mammalian parasitism, comprising: contacting a compound of any one of Formulae I or II with a enzyme selected from the group consisting of a bacterial PEPT enzyme, a fungal PEPT enzyme, a plant PEPT enzyme, a trypanosomal PEPT enzyme, a protozoan PEPT enzyme or any other non-mammalian organism expressing the PEPT enzyme; comparing the activity of the enzyme after the contacting with each compound of any one of Formula I or II to the activity of the enzyme before the contacting; and selecting a compound of any one of Formula I or II that changes the activity of the enzyme after the contacting.

In another aspect, disclosed herein is a method of modulating the activity of an enzyme that utilizes a phosphorylated molecule as a substrate.

In another aspect, disclosed herein is a method of modulating the activity of an enzyme that generates a phosphorylated molecule as a product.

In another aspect, disclosed herein is a method of modulating the activity of a kinase enzyme.

In another aspect, disclosed herein is a method of modulating the activity of a phosphatase enzyme.

In another aspect, disclosed herein is a method of modulating the activity of a receptor utilizing a phosphorylated molecule as a ligand.

In another aspect, disclosed herein is a method of modulating the activity of an enzyme utilizing a phosphorylated molecule as a cofactor.

In another aspect, disclosed herein is a method of modulating the activity of a macromolecule that has affinity for a phosphorylated molecule.

In another aspect, disclosed herein is a method of modulating the activity of a molecule that has affinity for a phosphorylated molecule.

EXAMPLES

The following examples are provided by way of illustration only and are not intended, nor should they be construed, as limiting the scope of this disclosure in any manner whatsoever.

Example 1

Computational Chemistry

The isostere disclosure was analyzed using ab initio calculations with density functional theory employing the B3LYP functional and the 6-31G* basis set (Yoo, H. Y. and Houk, K. N. JACS 119: 2877 (1997)). This method is known to provide excellent geometries and electrostatic potentials.

Phosphorylated tyrosine (phosphorylated 4-hydroxy phenylalanine) is known to play a key role in maintaining cellular homeostasis. A series of phospho-tyrosine analogues was computationally analyzed in order to obtain a deeper physiochemical understanding of the trifluoromethyl isostere and its coupling by various linkages to the parent phenyl ring. These calculations pointed to the remarkably and extremely similar shapes of the constant electron density surfaces in the case of the phenyl-linker-trifluoromethyl compounds as compared to the native phosphate. Overall electrostatic potentials are not identical due to the inherent charge of the phosphate group at physiological pH. These calculations clearly establish the trifluoromethyl functionality as a viable isostere for phosphate. The desired neutrality of the isostere is clear in these calculations while the overall lack of charge does not impact the constant electron density surface in comparison to the naturally occurring phosphate.

The energetics of solvation was examined across a wider set of trifluoromethyl analogues. The calculated dipole moments in aqueous solution for these compounds are presented along with the values for the neutral, monoanionic, and dianionic phenyl phosphates. In no case examined is the isostere found to be ionic. These results are presented in Table 1.

TABLE 1

Computationally Determined Solution Dipoles of Phosphorylated Tyrosine Analogues

| Compound | Solution Dipole (Debye) |
|---|---|
| $C_6H_5$—$OPO_3H_2$ | 1.0 |
| $C_6H_5$—$OPO_3H^-$ | 12.1 |
| $C_6H_5$—$OPO_3^-$ | 19.6 |
| $C_6H_5$—$CH_2CF_3$ | 3.1 |
| $C_6H_5$—$CF_2CF_3$ | 4.1 |
| $C_6H_5$—$S$—$CF_3$ | 3.8 |
| $C_6H_5$—$O$—$CF_3$ | 3.3 |
| $C_6H_5$—$CH_2PO_3H^-$ | 13.2 |
| $C_6H_5$—$CF_2PO_3H^-$ | 12.1 |
| $C_6H_5$—$SO_2$—$CF_3$ | 7.4 |
| $C_6H_5$—$NHSO_2$—$CF_3$ | 6.1 |
| 4-$CH_3$—$C_6H_4$—$S$—$CF_3$ | 4.4 |
| 4-$CH_3$—$C_6F_4$—$S$—$CF_3$ | 3.9 |

The generality of the isostere as a mimic of phosphate found beyond naturally occurring molecules was next examined. Dipole calculations analogous to those performed in the context of phospho-tyrosine were performed on the phosphorylated portion of the herbicide Glyphosate® [N-(phosphonomethyl) glycine, CAS1017-83-6] along with a set of trifluoromethyl-containing analogues. The ionics of the glyphosate molecule are well-known and these dipole calculations verify the similarity of the isostere to the phosphate. As in the case of the phospho-tyrosine analogues, the trifluoromethyl isostere was not ionized under any conditions explored by this calculation. These results are presented in Table 2.

TABLE 2

Computationally Determined Solution Dipoles of Glyphosate Fragment Analogues

| Compound | Solution Dipole (Debye) |
|---|---|
| $H_3N$—$CH_2$—$PO_3H_2$ | 6.5 |
| $H_2N$—$CH_2$—$PO_3H^-$ | 7.7 |
| $H_2N$—$CH_2$—$CF_3$ | 4.4 |
| $H_2N$—$CH_2$—$CH_2$—$CF_3$ | 3.4 |

Example 2

Chemical Preparations

Compounds Im ((2,2,2-trifluoro-ethylamino)-acetic acid) and In ([carboxymethyl-(2,2,2-trifluoro-ethyl)-amino]-acetic acid)

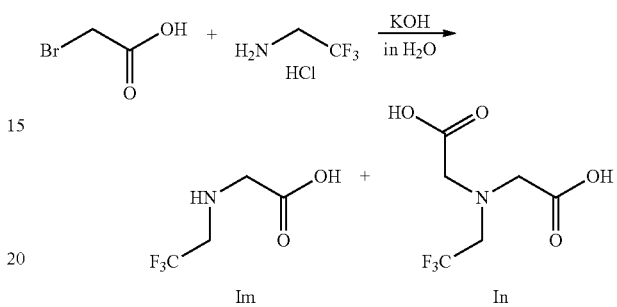

Trifluoroethylamine hydrochloride (8.19 g) was dissolved in water (5 mL), and the solution was adjusted to pH 9 with 1M aqueous KOH. Bromoacetic acid (2.78 g) was dissolved in water (10 ml), and the pH was adjusted to 9 with 1M aqueous KOH. This solution of bromoacetic acid was added in portions with stirring to the solution of the amine over 1 hour. The pH of the mixture was kept at 8-9 by addition of 1M KOH. The solution was left overnight at room temperature. In the morning the pH was 6.7; the solution was adjusted again to pH 9.5 with 1M KOH and the solution kept at pH 8.5-9 as above. After 1.5 hours, the reaction mixture was concentrated under vacuum (~30 mL), and the pH was adjusted again to 9. After 3 hours the solution was heated to 65° C. for 4 hours, cooled and left in the refrigerator overnight.

The next day, the pH was 7.2, and there was some precipitate. The pH was adjusted to 6 by addition of 2 M aqueous HBr, and the precipitate dissolved. A 0.1 ml aliquot was dried to a solid under vacuum, re-evaporated from $D_2O$, and dissolved in 0.7 ml $D_2O$. $^1H$ NMR and $^{13}C$ NMR showed the product as a mixture of Im and In in a ratio of 3:1.

The reaction mixture was analyzed by LC-MS. Approximately 1/50 of the solution was mixed with 1/10 of its volume 2M TEAA, and was injected on Gemini C18 20×250 mm column, and eluted with a gradient from 0 to 5% acetonitrile for 45 min at 10 ml/min. The target compound eluted late, and, after evaporation, 5 mg pure Im was obtained.

The reaction mixture was evaporated to dryness to leave 8.07 g of solid.

Sublimation

A 0.44 g sample of this solid was loaded in a sublimation apparatus, dried overnight under high vacuum at room temperature and sublimed by gradual increase from room temperature to 170° C. Sublimation began at approximately 85° C., and was fast above 100° C. The sublimate was dissolved in water/MeOH, and the solution evaporated to give 89.1 mg of pure Im. The residue was acidified with trifluoroacetic acid to approximately pH 2, evaporated to dryness, and resublimed. The sublimate consisted of 67 mg of Im, and the residue contained pure In.

Large-Scale Sublimation

The remaining solid (6.52 g) was sublimed as above. The flask was heated gradually to 150° C., and held at 150° C. for 30 minutes. The sublimate was dissolved in water/MeOH (~5.8 mL). An aliquot (0.3 mL) was evaporated to a semi-solid that solidified on standing to give 81.3 mg of Im. The balance of the sample was concentrated in the same manner to yield 4.80 g of Im as a white powder.

19

Characterization of Im:

¹H NMR: (D₂O) δ 3.79 (s, 2H), 3.87 (q, 2H).

¹³C NMR: (D₂O) δ 46.52 (four line pattern), 48.85, 121.99 (four line pattern), 169.81.

¹⁹F NMR: (D₂O) δ −68.82 (t, 3F).

Electrospray MS (negative ion): Calculated for C₄H₆F₃NO₂ [M-H]⁻ 156. Found 156.

Characterization of In:

¹H NMR: (D₂O) δ 3.91 (s, 4H), 3.93 (q, 2H).

Compound Io ((3,3,3-Trifluoro-propylamino)-acetic acid))

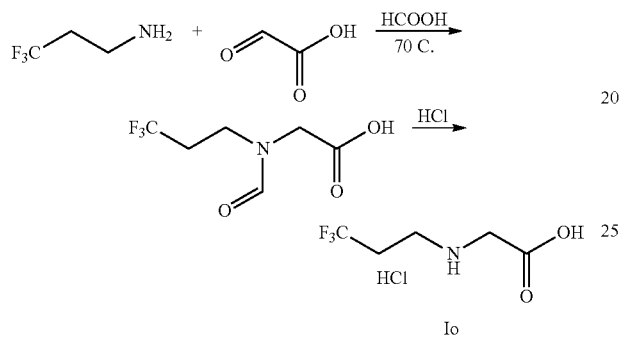

Trifluoropropylamine (0.46 g) was added with cooling to 98% formic acid (10 mL). Glyoxylic acid (0.78 g) was added, and the mixture was heated in a 50° C. water bath. After 16 hours, an aliquot (50 µl) was evaporated under vacuum, and the residue evaporated twice from 1 ml of D₂O. ¹H NMR showed ~10% unreacted amine and 90% of the formylated adduct.

Additional glyoxylic acid hydrate (0.078 g) was added, and the reaction mixture was heated at 75° C. in a water bath. After 2 hours an aliquot (50 µl) was evaporated and the residue evaporated from D₂O. ¹H NMR showed less amine present. After an additional 2.5 hours, the reaction mixture was evaporated, and the residue evaporated from water (5 ml), to give 1.15 g of clear oil.

The oil was dissolved in 1M aqueous HCl (8.1 mL), and the solution was heated at 95° C. for 2.5 hours. The ¹H NMR showed ca. 85% conversion to the deformylated product, Io. After refluxing for another 1.5 hours, the reaction mixture was left at room temperature overnight. The reaction mixture was evaporated to a semisolid. This material was dissolved in MeOH (~5 ml) and left in a freezer overnight. This suspension of crystals was reduced to ~2-3 mL, and diethyl ether (~10 ml) was added. This suspension was left at room temperature for 30 minutes and the crystalline precipitate was centrifuged and washed with 10 ml diethyl ether. The crystals were dried at high vacuum to give Io (0.88 g) as a white solid. A larger scale preparation was performed to give Io (3.10 g) as a white powder.

This process was developed from a similar approach (Kihlberg, J. et al Acta Chem Scan B 37: 911-916 (1983)).

Characterization of Io:

¹H NMR: (D₂O) δ 2.63 (m, 2H), 3.30 (t, 2H), 3.78 (s, 2H).

¹³C NMR: (D₂O) δ 30.05 (four line pattern), 40.73, 47.93, 125.38 (four line pattern), 168.93.

¹⁹F NMR: (D₂O) δ −65.65 (t, 3F).

Electrospray MS (negative ion): Calculated for C₅H₈F₃NO₂ [M-H]⁻ 170. Found 170.

20

Example 3

Example Chemical Preparations

Compound (Ic):

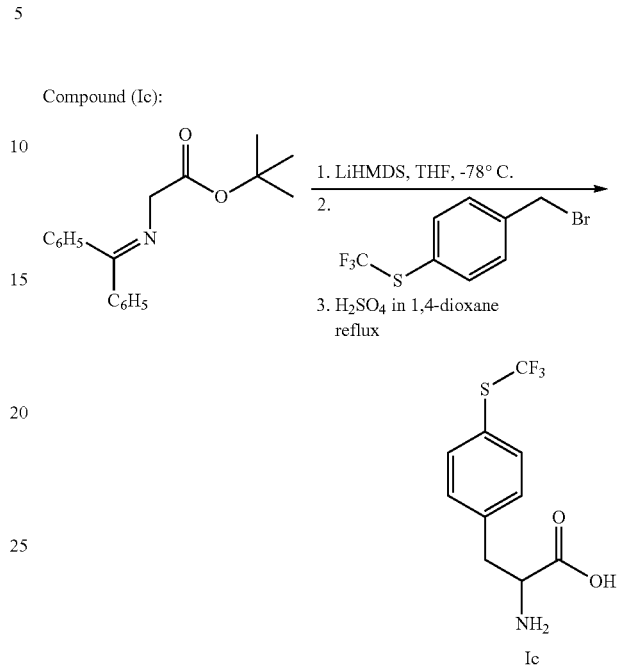

A 250-mL round-bottomed flask containing a large magnetic stirbar is charged with (benzhydrylidene-amino)-acetic acid tert-butyl ester (2.95 g) and dry THF (40 mL) under an atmosphere of nitrogen and cooled with stirring in a dry ice/acetone bath. A solution of LiHMDS (1.0 M in THF, 10 mL) is added via syringe and the content of the flask are stirred for 1 hour. A solution of 1-bromomethyl-4-trifluoromethylsulfanyl-benzene (2.71 g) in THF (10 mL) is added dropwise over 30 minutes. The cooling bath is removed and the contents of the flask are allowed to warm to ambient temperature. The reaction mixture is partitioned into Et₂O against an aqueous solution of 10% saturated citric acid (3×), an aqueous solution of 50% saturated sodium bicarbonate (3×) and brine. The organic solution is dried over sodium sulfate, the solids filtered and the resulting organic solution is concentrated to give the crude alkylation product. A 500-mL flask containing a magnetic stirbar is charged with this material, 1,4-dioxane (100 mL) and concentrated sulfuric acid (5.0 mL). The flask is fitted with a reflux condenser and the contents of the flask were heated to reflux for 12 h. The volatiles are removed in vacuo and the residue is recrystallized from ethyl acetate/hexanes.

Compounds (Id) wherein (R = H) and (Ie) wherein (R = CH3):

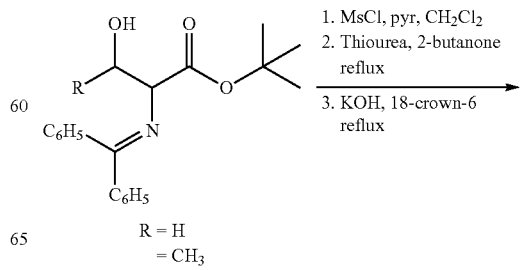

R = H
= CH₃

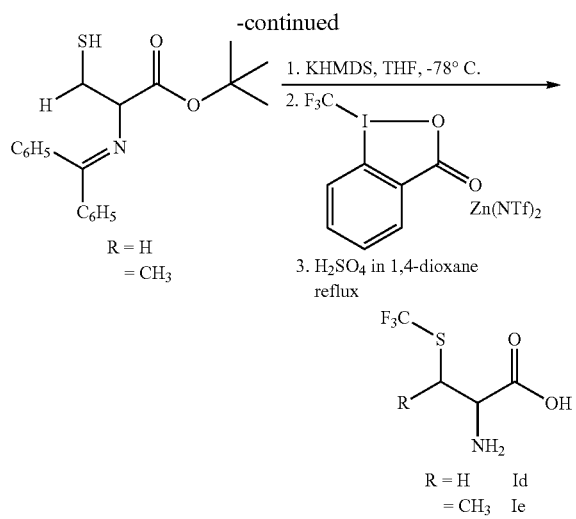

Compound (Id):

A 250-mL round-bottomed flask containing a large magnetic stirbar is charged with 2-(benzhydrylidene-amino)-3-hydroxy-propionic acid tert-butyl ester (3.25 g), pyridine (1.6 mL) and dry methylene chloride (50 mL) under an atmosphere of nitrogen and cooled with stiffing in an ice bath. A portion of mesyl chloride (1.15 g) is added and the contents of the flask are stirred for 1 hour. The volatile components of the reaction mixture are evaporated and the residue dissolved in 2-butanone (25 mL). Thiourea (1.52 gm) is added in a single portion, the flask is fitted with a reflux condenser and heated for 8 hours. Volatile components are again removed under vacuum and the residue is dissolved in THF (40 mL) and water (10 mL). Potassium hydroxide (1.40 g) and 18-crown-6 (0.26 g) are added to the solution and the contents are held at reflux overnight. The reaction mixture is cooled, partitioned into Et$_2$O against an aqueous solution of 10% saturated citric acid (3×), an aqueous solution of 50% saturated sodium bicarbonate (3×) and brine. The organic solution is dried over sodium sulfate, the solids filtered and the resulting organic solution is concentrated to give the crude thiol in suitable purity for the subsequent alkylation.

A 250-mL flask containing a magnetic stirbar is charged with 2-(benzhydrylidene-amino)-3-mercapto-propionic acid tert-butyl ester, and dry THF (40 mL) under an atmosphere of nitrogen and cooled with stirring in a dry ice/acetone bath. A solution of KHMDS (1.0 M in THF, 10 mL) is added via syringe and the content of the flask were held for 1 hour. A solution of 1-trifluoromethyl-1,2-benziodoxol-3-(1H)-one (3.16 g) in THF (10 mL) along with zinc triflimide (1.20 g) is added dropwise over 30 minutes. The cooling bath is removed and the contents of the flask are allowed to warm to ambient temperature. The reaction mixture is partitioned into Et$_2$O against an aqueous solution of 10% saturated citric acid (3×), an aqueous solution of 50% saturated sodium bicarbonate (3×) and brine. The organic solution is dried over sodium sulfate, the solids filtered and the resulting organic solution is concentrated to give the crude alkylation product. A 500-mL flask containing a magnetic stirbar is charged with this material, 1,4-dioxane (100 mL) and concentrated sulfuric acid (5.0 mL). The flask is fitted with a reflux condenser and the contents of the flask are held at reflux for 12 h. The volatiles are removed in vacuo and the residue is recrystallized from ethyl acetate/hexanes.

Compound (Ie):

A 250-mL round-bottomed flask containing a large magnetic stirbar is charged with 2-(benzhydrylidene-amino)-3-hydroxy-butyric acid tert-butyl ester (3.39 g) pyridine (1.6 mL) and dry methylene chloride (50 mL) under an atmosphere of nitrogen and cooled with stiffing in an ice bath. A portion of mesyl chloride (1.15 g) is added and the contents of the flask stirred for 1 hour. The volatile components of the reaction mixture are evaporated and the residue dissolved in 2-butanone (25 mL). Thiourea (1.52 gm) is added in a single portion, the flask fitted with a reflux condenser and heated for 8 hours. Volatile components are again removed under vacuum and the residue is dissolved in THF (40 mL) and water (10 mL). Potassium hydroxide (1.40 g) and 18-crown-6 (0.26 g) are added to the solution and the contents are held at reflux overnight. The reaction mixture is cooled, partitioned into Et$_2$O against an aqueous solution of 10% saturated citric acid (3×), an aqueous solution of 50% saturated sodium bicarbonate (3×) and brine. The organic solution is dried over sodium sulfate, the solids filtered and the resulting organic solution is concentrated to give the crude thiol in suitable purity for the subsequent alkylation.

A 250-mL flask containing a magnetic stirbar is charged with 2-(benzhydrylidene-amino)-3-mercapto-butyric acid tert-butyl ester, and dry THF (40 mL) under an atmosphere of nitrogen and cooled with stiffing in a dry ice/acetone bath. A solution of KHMDS (1.0 M in THF, 10 mL) is added via syringe and the content of the flask were held for 1 hour. A solution of 1-trifluoromethyl-1,2-benziodoxol-3-(1H)-one (3.16 g) in THF (10 mL) along with zinc triflimide (1.20 g) is added dropwise over 30 minutes. The cooling bath was removed and the contents of the flask are allowed to warm to ambient temperature. The reaction mixture is partitioned into Et$_2$O against an aqueous solution of 10% saturated citric acid (3×), an aqueous solution of 50% saturated sodium bicarbonate (3×) and brine. The organic solution is dried over sodium sulfate, the solids filtered and the resulting organic solution was concentrated to give the crude alkylation product. A 500-mL flask containing a magnetic stirbar is charged with this material, 1,4-dioxane (100 mL) and concentrated sulfuric acid (5.0 mL). The flask is fitted with a reflux condenser and the contents of the flask are held at reflux for 12 h. The volatiles are removed in vacuo and the residue is recrystallized from ethyl acetate/hexanes.

Compound (If):

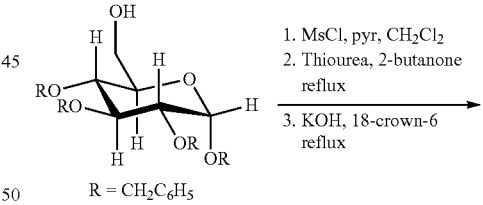

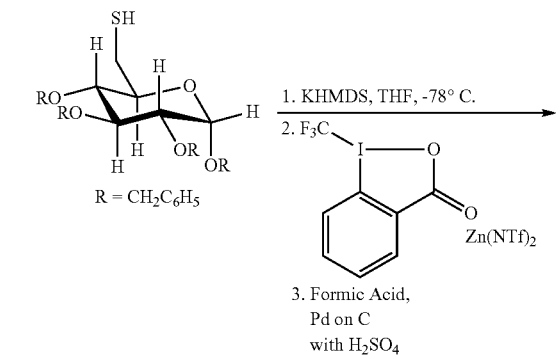

-continued

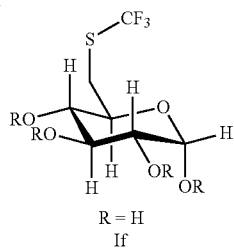

R = H
If

A 250-mL round-bottomed flask containing a large magnetic stirbar is charged with (3,4,5,6-tetrakis-benzyloxy-tetrahydro-pyran-2-yl)-methanol (5.40 g) pyridine (1.6 mL) and dry methylene chloride (50 mL) under an atmosphere of nitrogen and cooled with stirring in an ice bath. A portion of mesyl chloride (1.15 g) is added and the contents of the flask stirred for 1 hour. The volatile components of the reaction mixture are evaporated and the residue dissolved in 2-butanone (25 mL). Thiourea (1.52 gm) is added in a single portion, the flask is fitted with a reflux condenser and heated for 8 hours. Volatile components are again removed under vacuum and the residue dissolved in THF (40 mL) and water (10 mL). Potassium hydroxide (1.40 g) and 18-crown-6 (0.26 g) are added to the solution and the contents are held at reflux overnight. The reaction mixture is cooled, partitioned into Et$_2$O against an aqueous solution of 10% saturated citric acid (3×), an aqueous solution of 50% saturated sodium bicarbonate (3×) and brine. The organic solution is dried over sodium sulfate, the solids filtered and the resulting organic solution is concentrated to give the crude thiol in suitable purity for the subsequent alkylation.

A 250-mL flask containing a magnetic stirbar is charged with (3,4,5,6-tetrakis-benzyloxy-tetrahydro-pyran-2-yl)-methanethiol and dry THF (40 mL) under an atmosphere of nitrogen and cooled with stiffing in a dry ice/acetone bath. A solution of KHMDS (1.0 M in THF, 10 mL) is added via syringe and the content of the flask are held for 1 hour. A solution of 1-trifluoromethyl-1,2-benziodoxol-3-(1H)-one (3.16 g) in THF (10 mL) along with zinc triflimide (1.20 g) is added dropwise over 30 minutes. The cooling bath is removed and the contents of the flask are allowed to warm to ambient temperature. The reaction mixture is partitioned into Et$_2$O against an aqueous solution of 10% saturated citric acid (3×), an aqueous solution of 50% saturated sodium bicarbonate (3×) and brine. The organic solution is dried over sodium sulfate, the solids filtered and the resulting organic solution is concentrated to give the crude alkylation product. A 500-mL flask containing a magnetic stirbar is charged with this material, methanol (50 mL), and 10% Pd/C (0.5 g) under a nitrogen atmosphere. The flask is sealed and acetic acid (10 mL), sulfuric acid (2 mL) and formic acid (10 mL) are sequentially added via syringe. The contents of the flask are stirred at ambient temperature for 24 hours. The suspension is filtered and the resultant solution is concentrated to dryness. The product is recrystallized from ethyl acetate/hexanes.

Compound (Ig):

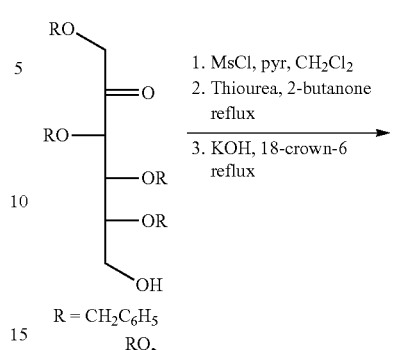

R = CH$_2$C$_6$H$_5$

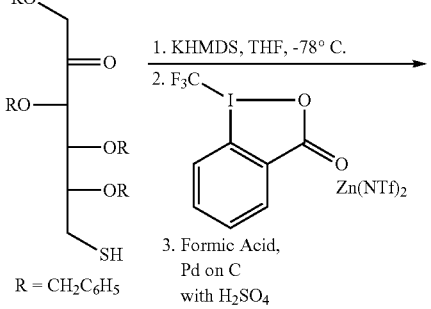

R = CH$_2$C$_6$H$_5$

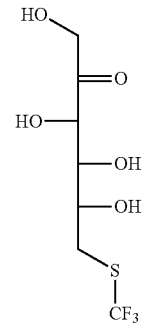

Ig

A 250-mL round-bottomed flask containing a large magnetic stirbar is charged with 1,3,4-tris-benzyloxy-5-hydroxymethyl-6-phenoxy-hexan-2-one (5.40 g) pyridine (1.6 mL) and dry methylene chloride (50 mL) under an atmosphere of nitrogen and cooled with stirring in an ice bath. A portion of mesyl chloride (1.15 g) is added and the contents of the flask stirred for 1 hour. The volatile components of the reaction mixture are evaporated and the residue dissolved in 2-butanone (25 mL). Thiourea (1.52 gm) is added in a single portion and the flask is fitted with a reflux condenser and heated for 8 hours. Volatile components are again removed under vacuum and the residue dissolved in THF (40 mL) and water (10 mL). Potassium hydroxide (1.40 g) and 18-crown-6 (0.26 g) are added to the solution and the contents are held at reflux overnight. The reaction mixture is cooled, partitioned into Et$_2$O against an aqueous solution of 10% saturated citric acid (3×), an aqueous solution of 50% saturated sodium bicarbonate (3×) and brine. The organic solution is dried over sodium sulfate, the solids filtered and the resulting organic solution is concentrated to give the crude thiol in suitable purity for the subsequent alkylation.

A 250-mL flask containing a magnetic stirbar is charged with 1,3,4-tris-benzyloxy-5-mercaptomethyl-6-phenoxy-hexan-2-one and dry THF (40 mL) under an atmosphere of nitrogen and cooled with stiffing in a dry ice/acetone bath. A solution of KHMDS (1.0 M in THF, 10 mL) is added via syringe and the content of the flask are held for 1 hour. A solution of 1-trifluoromethyl-1,2-benziodoxol-3-(1H)-one (3.16 g) in THF (10 mL) along with zinc triflimide (1.20 g) is added dropwise over 30 minutes. The cooling bath is removed and the contents of the flask are allowed to warm to ambient temperature. The reaction mixture is partitioned into Et$_2$O against an aqueous solution of 10% saturated citric acid (3×), an aqueous solution of 50% saturated sodium bicarbonate (3×) and brine. The organic solution is dried over sodium sulfate, the solids filtered and the resulting organic solution is concentrated to give the crude alkylation product. A 500-mL flask containing a magnetic stirbar is charged with this material, methanol (50 mL), and 10% Pd/C (0.5 g) under a nitrogen atmosphere. The flask is sealed and acetic acid (10 mL), sulfuric acid (2 mL) and formic acid (10 mL) are sequentially added via syringe. The contents of the flask are stirred at ambient temperature for 24 hours. The suspension is filtered and the resultant solution concentrated to dryness. The product is recrystallized from ethyl acetate/hexanes.

are held at reflux overnight. The reaction mixture is cooled, partitioned into Et$_2$O against an aqueous solution of 10% saturated citric acid (3×), an aqueous solution of 50% saturated sodium bicarbonate (3×) and brine. The organic solution is dried over sodium sulfate, the solids filtered and the resulting organic solution is concentrated to give the crude thiol in suitable purity for the subsequent alkylation.

A 250-mL flask containing a magnetic stirbar is charged with 2-(benzhydrylidene-amino)-3-(tert-butyl-dimethyl-silanyloxy)-octadec-4-ene-1-thiol and dry THF (40 mL) under an atmosphere of nitrogen and cooled with stirring in a dry ice/acetone bath. A solution of KHMDS (1.0 M in THF, 10 mL) is added via syringe and the content of the flask were held for 1 hour. A solution of 1-trifluoromethyl-1,2-benziodoxol-3-(1H)-one (3.16 g) in THF (10 mL) along with zinc triflimide (1.20 g) is added dropwise over 30 minutes. The cooling bath is removed and the contents of the flask are allowed to warm to ambient temperature. The reaction mixture is partitioned Compound (Ih):

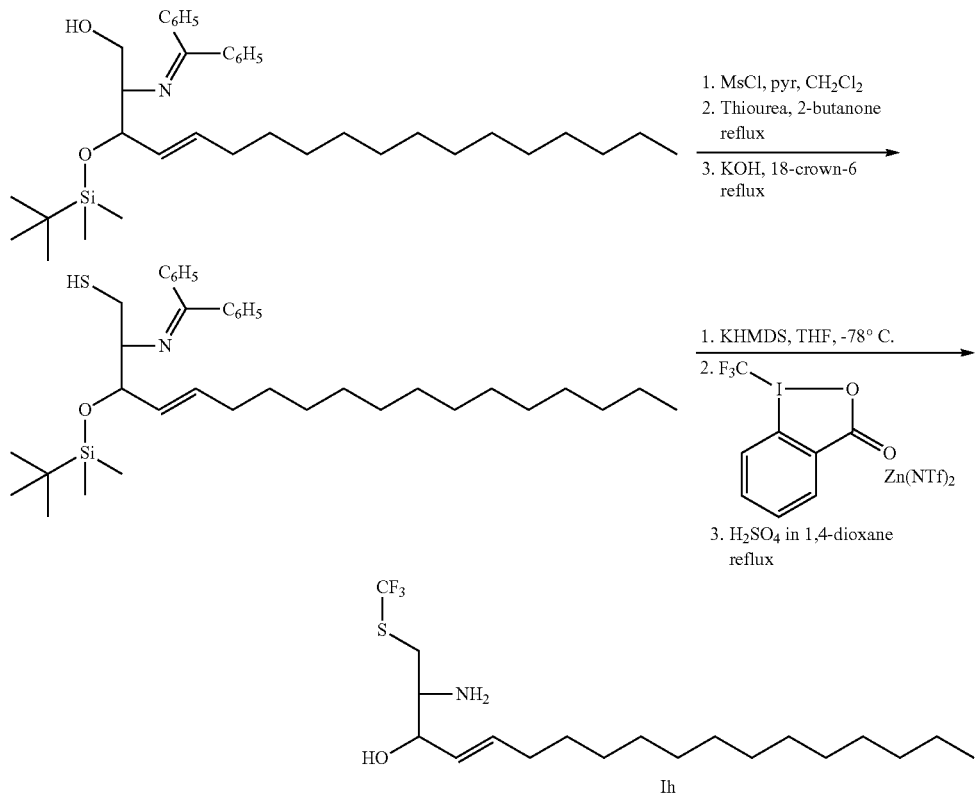

A 250-mL round-bottomed flask containing a large magnetic stirbar is charged with 2-(benzhydrylidene-amino)-3-(tert-butyl-dimethyl-silanyloxy)-octadec-4-en-1-ol (5.78 g), pyridine (1.6 mL) and dry methylene chloride (50 mL) under an atmosphere of nitrogen and cooled with stirring in an ice bath. A portion of mesyl chloride (1.15 g) is added and the contents of the flask stirred for 1 hour. The volatile components of the reaction mixture are evaporated and the residue dissolved in 2-butanone (25 mL). Thiourea (1.52 gm) is added in a single portion, the flask fitted with a reflux condenser and heated for 8 hours. Volatile components are again removed under vacuum and the residue dissolved in THF (40 mL) and water (10 mL). Potassium hydroxide (1.40 g) and 18-crown-6 (0.26 g) are added to the solution and the contents into Et$_2$O against an aqueous solution of 10% saturated citric acid (3×), an aqueous solution of 50% saturated sodium bicarbonate (3×) and brine. The organic solution is dried over sodium sulfate, the solids filtered and the resulting organic solution was concentrated to give the crude alkylation product. A 500-mL flask containing a magnetic stirbar is charged with this material, methanol (50 mL), and 10% Pd/C (0.5 g) under a nitrogen atmosphere. The flask is sealed and acetic acid (10 mL), sulfuric acid (2 mL) and formic acid (10 mL) are sequentially added via syringe. The contents of the flask are stirred at ambient temperature for 24 hours. The suspension is filtered and the resultant solution concentrated to dryness. The product is recrystallized from ethyl acetate/hexanes.

Compound (Ii):

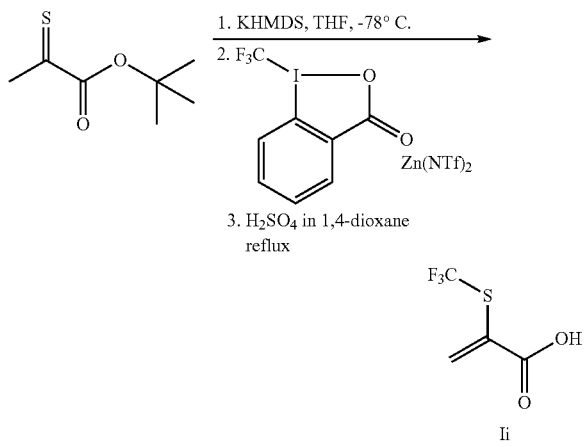

A 250-mL flask containing a magnetic stirbar is charged with 2-thioxo-propionic acid tert-butyl ester (1.60 g), and dry THF (40 mL) under an atmosphere of nitrogen and cooled with stiffing in a dry ice/acetone bath. A solution of KHMDS (1.0 M in THF, 10 mL) is added via syringe and the content of the flask are held for 1 hour. A solution of 1-trifluoromethyl-1,2-benziodoxol-3-(1H)-one (3.16 g) in THF (10 mL) along with zinc triflimide (1.20 g) is added dropwise over 30 minutes. The cooling bath was removed and the contents of the flask were allowed to warm to ambient temperature. The reaction mixture is partitioned into Et$_2$O against an aqueous solution of 10% saturated citric acid (3×), an aqueous solution of 50% saturated sodium bicarbonate (3×) and brine. The organic solution is dried over sodium sulfate, the solids filtered and the resulting organic solution is concentrated to give the crude alkylation product. A 500-mL flask containing a magnetic stirbar is charged with this material, 1,4-dioxane (100 mL) and concentrated sulfuric acid (5.0 mL). The flask is fitted with a reflux condenser and the contents of the flask are held at reflux for 12 h. The volatiles are removed in vacuo and the residue is recrystallized from ethyl acetate/hexanes.

Compound (Ij):

A 250-mL flask containing a magnetic stirbar is charged with (N-methyl-guanidino)-acetic acid tert-butyl ester (1.87 g), and dry THF (40 mL) under an atmosphere of nitrogen and cooled with stiffing in a dry ice/acetone bath. A solution of KHMDS (1.0 M in THF, 10 mL) is added via syringe and the content of the flask are held for 1 hour. A solution of 1-trifluoromethyl-1,2-benziodoxol-3-(1H)-one (3.16 g) in THF (10 mL) along with zinc triflimide (1.20 g) is added dropwise over 30 minutes. The cooling bath was removed and the contents of the flask are allowed to warm to ambient temperature. The reaction mixture is partitioned into Et$_2$O against an aqueous solution of 10% saturated citric acid (3×), an aqueous solution of 50% saturated sodium bicarbonate (3×) and brine. The organic solution is dried over sodium sulfate, the solids filtered and the resulting organic solution is concentrated to give the crude alkylation product. A 500-mL flask containing a magnetic stirbar is charged with this material, 1,4-dioxane (100 mL) and concentrated sulfuric acid (5.0 mL). The flask is fitted with a reflux condenser and the contents of the flask are held at reflux for 12 h. The volatiles are removed in vacuo and the residue is recrystallized from ethyl acetate/hexanes.

Compound (Ik):

A 250-mL round-bottomed flask is charged with a large stirbar, 1,1,2-tri-benzylpyrophosphoryl chloride (4.67 g), pyridine (1.6 mL), dry methylene chloride (50 mL) and is sealed under an atmosphere of nitrogen and cooled with stirring in an ice/salt bath. A portion of trifluoromethylsulfide (1.12 g) is added dropwise (Caution: STENCH) over 1 hour and the contents of the flask are allowed to warm for 1 hour. All volatile materials are removed under vacuum. The residue is taken up with methanol (50 mL), and 10% Pd/C (0.5 g) is added under a nitrogen atmosphere. The flask is sealed and acetic acid (10 mL), sulfuric acid (2 mL) and formic acid (10 mL) are sequentially added via syringe. The contents of the flask are stirred at ambient temperature for 24 hours. The suspension is filtered and the resultant solution concentrated to dryness. This material is dissolved in methylene chloride (40 mL) and pyridine (10 mL) and the flask is sealed under an atmosphere of nitrogen. The contents are cooled in an ice bath with stirring and thionyl chloride (1.20 g) is added dropwise over 30 minutes followed by a solution of 2-(6-amino-purin-9-yl)-5-hydroxymethyl-tetrahydro-furan-3,4-diol (2.67 g) in THF (20 mL). The reaction mixture is allowed to warm to ambient temperature, poured onto ice water and partitioned into Et$_2$O. The combined Et$_2$O extracts are washed with water (3×), dried over sodium sulfate, the solids filtered and the resulting organic solution is concentrated to give the product.

Compound (II):

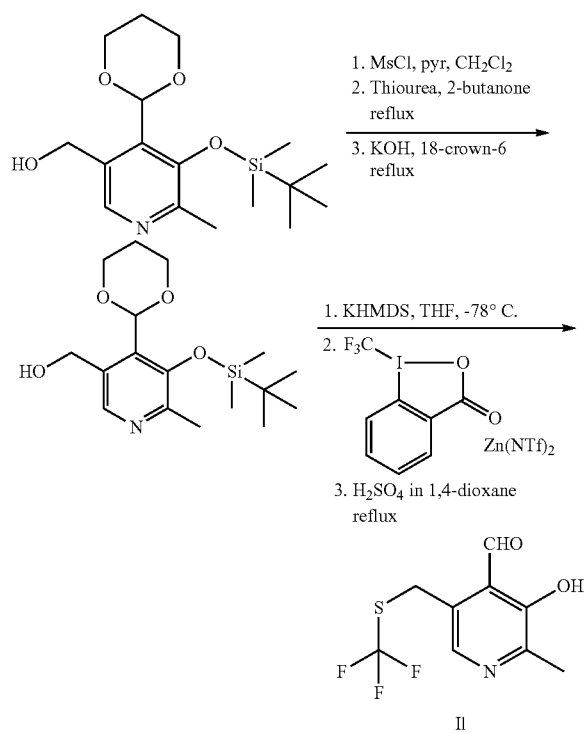

A 250-mL round-bottomed flask containing a large magnetic stirbar is charged with [5-(tert-butyl-dimethyl-silanyloxy)-4-[1,3]dioxan-2-yl-6-methyl-pyridin-3-yl]-methanol (3.40 g), pyridine (1.6 mL) and dry methylene chloride (50 mL) under an atmosphere of nitrogen and cooled with stirring in an ice bath. A portion of mesyl chloride (1.15 g) is added and the contents of the flask are stirred for 1 hour. The volatile components of the reaction mixture are evaporated and the residue dissolved in 2-butanone (25 mL). Thiourea (1.52 gm) is added in a single portion and the flask is fitted with a reflux condenser and heated for 8 hours. Volatile components are again removed under vacuum and the residue is dissolved in THF (40 mL) and water (10 mL). Potassium hydroxide (1.40 g) and 18-crown-6 (0.26 g) are added to the solution and the contents are held at reflux overnight. The reaction mixture is cooled, partitioned into Et$_2$O against an aqueous solution of 10% saturated citric acid (3×), an aqueous solution of 50% saturated sodium bicarbonate (3×) and brine. The organic solution is dried over sodium sulfate, the solids filtered and the resulting organic solution is concentrated to give the crude thiol in suitable purity for the subsequent alkylation.

A 250-mL flask containing a magnetic stirbar is charged with [5-(tert-butyl-dimethyl-silanyloxy)-4-[1,3]dioxan-2-yl-6-methyl-pyridin-3-yl]methane-thiol and dry THF (40 mL) under an atmosphere of nitrogen and cooled with stirring in a dry ice/acetone bath. A solution of KHMDS (1.0 M in THF, 10 mL) is added via syringe and the content of the flask were held for 1 hour. A solution of 1-trifluoromethyl-1,2-benziodoxol-3-(1H)-one (3.16 g) in THF (10 mL) along with zinc triflimide (1.20 g) is added dropwise over 30 minutes. The cooling bath was removed and the contents of the flask are allowed to warm to ambient temperature. The reaction mixture is partitioned into Et$_2$O against an aqueous solution of 10% saturated citric acid (3×), an aqueous solution of 50% saturated sodium bicarbonate (3×) and brine. The organic solution is dried over sodium sulfate, the solids filtered and the resulting organic solution is concentrated to give the crude alkylation product. A 500-mL flask containing a magnetic stirbar is charged with this material, methanol (50 mL), and 10% Pd/C (0.5 g) under a nitrogen atmosphere. The flask is sealed and acetic acid (10 mL), sulfuric acid (2 mL) and formic acid (10 mL) are sequentially added via syringe. The contents of the flask are stirred at ambient temperature for 24 hours. The suspension is filtered and the resultant solution concentrated to dryness. The product is recrystallized from ethyl acetate/hexanes.

Example 4

Enzymatic Assays

Compounds were evaluated in enzymatic assays against two phospho-enolpyruvyl transferases (PEPTs):
EPSPS (AroA gene product) EC: 2.5.1.19
MurA gene product EC: 2.5.1.7
Procedure:
Compounds were dissolved in water at 100 mg/mL. Enzyme reactions were conducted in 100 ml 50 mM HEPES (pH 7.5) at room temperature. The reaction was started by the addition of EPSPS or MurA into buffer containing 100 µM PEP, 100 µM S3P or 100 µM UNAG and 0, 1, 10, 100, 1000 µg/ml of the respective compound. Glyphosate and/or fosfomycin were used as control. The reactions were stopped after 3 minutes by the addition of 800 µL of Malachite green reagent. Color development was allowed to proceed for 5 min and stopped by the addition of 100 µL 34% sodium citrate. The optical density was measured at 650 nm and the activity was calculated using phosphate standard.
Results:
Enzyme activity is expressed in percentage of the respective control (minus inhibitor) in FIG. 1, where MEH-001 is 2,2,2-trifluoro-ethylamino-acetic acid), MEH-001B is [Carboxymethyl-(2,2,2-trifluoro-ethyl)-amino]-acetic acid, and MEH-002 is (3,3,3-trifluoro-propylamino)-acetic acid.

Example 5

Cellular Assays and Cytotoxicity Studies

Compounds were evaluated in cellular assays against four pathogens:
*Trypanosoma brucei* rhodesiense
*Trypanosoma cruzi* Tulahuen
*Leishmania donovani*
*Plasmodium falciparum*
Cytotoxicity evaluations were also performed using rat skeletal myoblast cells. Experimental assay protocols and the cytotoxicity protocol appear below. Assay and cytotoxicity results appear in Table 3.
In Vitro Sensitivity Assays: African Trypanosomes (LILIT, Alamar Blue)
Standard Parasite Strains: *Trypanosoma brucei* rhodesiense; STIB 900

Standard Drug: Melarsoprol™ (Main standard for STIB 900)
Standard Conditions:
Medium: T.b. rhodesiense,
Per 100 mL: 83 mL MEM
1 mL Balz-components (Balz et al., 1985)
2-Mercaptoethanol: 1 mL of a diluted stock (14 μL 2-mercaptoethanol+10 mL $dH_2O$)
15 mL heat inactivated horse serum (15% final concentration)
Plates: Costar™ 96-well microtitre plates
Incubation: 37° C., 5% $CO_2$
Definition of test score:
inactive: $IC_{50}$>3 μg/ml
moderate activity: 0.2 μg/ml<$IC_{50}$<3 μg/ml
high activity: $IC_{50}$<0.2 m/ml (for active series<0.1)
Melarosprol (in STIB 900): average $IC_{50}$=0.004
Drug Preparation:
Compounds are dissolved in DMSO at 10 mg/ml (SOP Nr. If insoluble other solvents are used according to the recommendations of the supplier. The DMSO stocks are kept at −20° C. For the assays fresh dilutions in medium are prepared each time. (Since DMSO is toxic, care has to be taken not to exceed a final concentration of 1% DMSO in the assay).
Procedure:
1. Into the wells H1 and H12 add 75 μl medium and into well H2-H11 add 75 μl of medium that contains two times the highest drug concentration desired. Per plate 10 drugs can be tested (drug 1-10 column 2-11). For each assay melarsoprol is tested as the standard with 0.072 μg/ml as highest concentration.
2. Add 50 μl of medium at room temperature to rows A to G of a 96-well plate (row H has the drug).
3. Serial drug dilutions are prepared by using a 12-well multi-pipette. First, remove 25 μl from wells of row H and put it into row G and mix well. Next, 25 μl are taken out of row G and put into row F and so on until row B. The last 25 μl of row B are discarded. A serial dilution factor of 1:3 is thus obtained. Row A wells serve as controls without drugs.
4. 50 μl of medium without trypanosomes are added to columns 1 and 12; these columns serve as background controls.
5. Dilute the trypanosomes to 3×104 tryps/ml. The trypanosome density is adjusted with a Cell Analysis System (CASY, Scharfe System) or by a count on the haemocytometer. (The trypanosome density used should be adjusted depending on the current growth characteristics of the corresponding cultures) Per plate, allow for the use of 3.5 ml of the trypanosome stock.
6. Into the remaining wells (column 2-11), add 50 μl of trypanosome suspension.
7. The plates are then incubated for 69 h (=72 h—time incubated with Resazurin)* at 37° C./5% $CO_2$.
Evaluation
1. The plates are inspected under an inverted microscope to ensure that growth is normal. Additional information may be recorded, such as drug insolubility or contamination, etc.
2. Add 10 μl of the fluorescent dye Resazurin to each well and incubate for an additional 3 hours (until a subtle color change is observed, but maximum 5 hours)*.
3. To determine an $IC_{50}$ value, the plate is read at excitation wavelength 530 nm and emission wavelength 590 nm (pre-set LILIT template file). Make sure that the values in each well are approximately 10 times the background values.
4. Data are transferred into a graphic program (Excel) and are evaluated to determine the $IC_{50}$ or analyzed using the fluorescent plate reader software (SoftMax).
In Vitro Sensitivity Assays: T. cruzi
Standard assay parasite strains: T. cruzi Tulahuen C2C4, containing the Lac Z gene.
Standard Cell line: L-6 cells (mouse muscle fibroblasts)

Standard Drug: Benznidazole (Radanil™, Hoffman La Roche): start conc. 30 μg/ml ($IC_{50}$=0.35 μg/ml)
Standard Conditions:
Medium: RPMI 1640+10% FCS+1.7 μM L-Glutamine (850 μl 200 mM for 100 ml)
Plates: Costar™ 96-well microtiter plates
Incubation: 37° C., 5% $CO_2$
Substrate: 2.5×CPRG/Nonidet Solution: 5× stock=500 μl Nonidet P40+30.38 mg CPRG in 100 ml 1×PBS
Dilute the 5× stock 1:1 with 1×PBS.
Light Sensitive!
Definition of test score:
inactive: $IC_{50}$>30 μg/mL
moderate activity: 2 μg/mL<$IC_{50}$<30 m/mL
high activity: $IC_{50}$<2 μg/mL (active series <1 μg/mL)
Drug Preparation:
Compounds are dissolved in DMSO at 10 mg/ml (SOP Nr. If insoluble other solvents are used according to the recommendations of the supplier. The DMSO stocks are kept at −20° C. For the assays fresh dilutions in medium are prepared each time. (Since DMSO is toxic, care has to be taken not to exceed a final concentration of 1% DMSO in the assay).
CAUTION: T. cruzi is a human pathogen and must be treated as such, i.e. Biohazard waste, soap disinfection, gloves.
Procedure:
Day 1:
Seed all 96 wells with 100 μl medium containing 2×103 L6 cells per well, using a multiwall repeater pipette.
9.6 ml per plate
2×104 L-6 cells/ml . . . 100 μl per well
Day 2:
Add 5×103 tryps into all columns 2-11 using the multi-well repeater pipette. In columns 1 and 12, add 50 μl of medium.
3.2 ml of trypanosome suspension per plate
1×105 tryps/ml . . . 50 μl per well
Day 4:
Remove medium from wells in row A to G with the aspirator and replace with 100 μl medium using the multi-well repeater pipette. (Take care to not cross infect columns 1 and 12-remove medium only before medium+tryps!) Remove medium from row H (do not cross-infect!) and add 150 μl medium to wells H1 and H12 and add into wells H2-H11 150 μl medium with the highest drug concentration. Per plate 10 drugs can be tested (drug 1 10 columns 2-11). Note: Do the first half of the plates (remove medium and add drug) and then the second half, so the cells/tryps don't dry out. Serial drug dilutions are prepared by using a 12-channel multi-pipette. First, remove 50 μl from wells of row H and put into row G and mix well. Next, 50 μl are taken out of row G and put into row F and so on until row B. The last 50 μl of row B are discarded. A serial dilution factor of 1:3 is thus obtained. Wells in row A serve as control wells without drugs.
Day 8:
Evaluate the plates visually to determine the MIC (Minimal Inhibitory Concentration): lowest drug concentration at which no trypanosomes with a normal morphology and motility as compared to the control wells can be seen. 50 μl of 2.5×CPRG/Nonidet are added to all wells. A color reaction will become visible in 2-6 hours and can be read in an Absorbance Reader at 540 nm Data are transferred into a graphic program (Excel) and are evaluated to determine the $IC_{50}$ or analyzed using the plate reader software (SoftMax).
In Vitro Sensitivity Assays: Axenic Leishmania donovani
Standard parasite strains: L. donovani MHOM-ET-67/L82, axenic amastigotes
Standard drug: Miltefosin
Standard conditions:
Medium: SM, pH 5.4 plus 10% heat inactivated FCS
Plates: Costar™ 96-well microtitre plates
Incubation: 37° C., 5% $CO_2$, 72 hours Definition of test score:
no activity (no repeat): $IC_{50}$>3 µg/ml
low activity (repeat): 0.5<$IC_{50}$<3 µg/ml
high activity (repeat): $IC_{50}$<0.5 µg/ml
Miltefosin: average $IC_{50}$=0.131 µg/ml Drug Preparation:

Compounds are dissolved in DMSO(SOP Nr. D1), unless otherwise specified by the supplier. The stock solution is 10 mg/ml and stored at −20° C. Stocks are kept for 3 years. (Since DMSO is toxic, care has to be taken not to exceed a final concentration of 1% DMSO in the assay).

Procedure:

1. Into the wells H1 and H12 add 75 µl of medium and into well H2-H11 add 75 µl of medium that contains two times the highest drug concentration desired. Per plate 10 drugs can be tested (drug 1-10 column 2-11). For each assay Miltefosin is tested as the standard with 3 µg/ml as highest concentration.

2. Add 50 µl of medium at room temperature to rows A to G of a 96-well plate (row H has the drug).

3. Serial drug dilutions are prepared by using a 12-channel multi-pipette. First, remove 25 µl from wells of row H and put it into row G and mix well. Next, 25 µl are taken out of row G and put into row F and so on until row B. The last 25 µl of row B are discarded. A serial dilution factor of 1:3 is thus obtained. Row A wells serve as controls without drugs.

4. 50 µl of medium without parasites are added to columns 1 and 12 which serve as controls to provide the background signal in the fluorescence scanner.

5. 50 µl of a suspension containing 2×106 axenically grown amastigotes from a healthy culture in log phase are added to all the remaining wells leading to an initial parasite density of 1×106/ml.

6. The plates are incubated for 70 hours (=72 h—time incubated with Resazurin) at 37° C./5% $CO_2$.

Evaluation

1. The plates are inspected under an inverted microscope to ensure that growth is normal. Additional information may be recorded, such as drug insolubility or contamination, etc.

2. Add 10 µl of the fluorescent dye Resazurin to each well and incubate for an additional 2 hours (until a subtle color change is observed).

3. To determine an $IC_{50}$ value, the plate is read in a fluorescence scanner (SPECTRAmax GEMINI XS from Molecular Devices) at excitation wavelength 530 nm and emission wavelength 590 nm (pre-set LILIT template file). Make sure that the values in each well are approximately 10 times the background values.

4. Data are transferred into a graphic program (Excel) and are evaluated to determine the $IC_{50}$ or analyzed using the fluorescent plate reader software (SoftMax).

In Vitro Sensitivity Assays: *Plasmodium falciparum* ($^3$H-hypoxanthine Incorporation)

Standard assay parasite strains:
*Plasmodium falciparum* NF54 (sensitive to all known drugs)
*Plasmodium falciparum* $K_1$ (Chloroquine/Pyrimethamine resistant)

Standard Drugs:
Chloroquine (10 mg/ml stock; start concentration 1000 ng/ml) (average $IC_{50}$: 0.065 µg/ml)
Artemisinine (Qinghaosu) (5 mg/ml stock; start concentration 10 ng/ml)

Standard Conditions:
Medium: RPMI 1640 without hypoxanthine 10.44 g/L
HEPES 5.94 g/L
Albumax® 5 g/L
Neomycin 10 ml/L (100 U/ml)
NaHCO3 50 g/L stock 42 ml/L (2.1 g/L)
Radioactive Hypoxanthine: 500 µl 3H-hypoxanthine stock+500 µl EtOH+49 ml medium (these 1 ml aliquots are stored at −20° C., medium added fresh)
Washed human red blood cells A+(RBC): May be stored up to 10 days
Fresh dilutions made for each assay
Plates: Costar™ 96-well microtitre plates
Incubation: 37° C., 4% $CO_2$, 3% $O_2$, 93% $N_2$ Definition of test score:
inactive (no repeat): $IC_{50}$>5 µg/ml
moderate activity (repeat): 0.5 µg/ml<$IC_{50}$<5 µg/ml
high activity (repeat): $IC_{50}$<0.5 µg/ml (for active series<0.2)

Drug preparation:

Compounds are dissolved in DMSO at 10 mg/ml (SOP Nr. D1). If insoluble other solvents are used according to the recommendations of the supplier. The DMSO stocks are kept at −20° C. For the assays fresh dilutions in medium are prepared each time. (Since DMSO is toxic, care has to be taken not to exceed a final concentration of 0.5% DMSO in the assay).

CAUTION: *P. falciparum* is a human pathogen and must be treated as such, i.e. Biohazard waste, disinfection, gloves, etc.

Procedure:

Day 1

1. Into the wells of row H add 100 µl of medium that contains four times the highest drug concentration desired. Per plate 12 drugs can be tested.

2. Add 100 µl of medium at room temperature to all wells of the plate.

3. Serial drug dilutions are prepared by using a 12-well multi-pipette. First, remove 100 µl from wells of row H and put it into row G and mix well. Next, 100 µl are taken out of row G and put into row F and so on until row B. The last 100 µl of row B are discarded. A serial dilution factor of 1:2 is thus obtained. Row A wells serve as controls without drugs.

4. 100 µl of medium+RBC are added to the last 4 wells of row A; these columns serve as background controls (that may be caused by 3H-hypoxanthine incorporation into RBC without the parasite)

5. Into the remaining wells, add 100 µl of medium+RBC+ *P. falciparum* mix.

6. The plates are put into a chamber and gassed with a 4% $CO_2$, 3% $O_2$, 93% N2 mix. The chamber is placed in the incubator for 48 hours at 37° C.

Day 3

1. Add 50 µl of medium+3H-hypoxanthine (0.5 µCi) to each well.

2. The plates are put back into the chamber and gassed with a 4% $CO_2$, 3% $O_2$, 93% N2 mix. The chamber is placed back in the incubator for 24 hours at 37° C.

Day 4: Evaluation

Data are transferred into a graphic program (Excel) and are evaluated to determine the $IC_{50}$.

In Vitro Sensitivity Assays: Cytotoxicity
Standard Cell Lines:
L-6 (rat skeletal myoblast cells) or HT-29 (human bladder carcinoma)
Standard Drug: Podophylotoxin (PPT); starting concentration: 0.1 µg/ml average $IC_{50}$=0.006 µg/ml Standard Conditions:
Medium: RPMI 1640+10% FCS+1.7 µM L-Glutamine (850 µl 200 mM for 100 ml)
Culture vessel: Costar™ 96-well microtiter plates
Incubation: 37° C., 5% $CO_2$ Drug Preparation:

Compounds are dissolved in DMSO(SOP Nr. D1), unless otherwise specified by the supplier. The stock solution is 10 mg/ml and stored at −20° C. Stocks are kept for 3 years. (Since DMSO is toxic, care has to be taken not to exceed a final concentration of 1% DMSO in the assay).

Procedure:

1. Add 100 μl of medium to wells of columns 1 and 12 of a microtiter plate. These wells serve as controls.

2. 100 μl of a cell suspension of 4×104 cells/m$^1$ is added into the remaining columns (2-11). Cells are allowed to attach over night. Per plate, allow for 6.5 ml of cell suspension to be used.

3. The next day, the medium is removed from row H (do this for half of the plates and go to step 4 and return to step 3 for the second half, so the cells don't dry out).

4. 150 μl of medium containing the highest drug concentration is added to the wells H2-H11 and 150 μl medium is added in wells H1 and H12. 10 drugs can be tested on one plate (drug 1-10 in column 2-11). Columns 1 and 12 serve as background.

5. Serial drug dilutions are prepared by using a 12-channel multi-pipette. First, remove 50 μl from wells of row H and put into row G and mix well. Next, 50 μl are taken out of row G and put into row F and so on until row B. The last 50 μl of row B are discarded. A serial dilution factor of 1:3 is thus obtained. Wells in row A serve as control wells without drugs.

6. The plates are then incubated for 70 hrs at 37° C./5% $CO_2$.

Evaluation:

1. The plates are inspected under an inverted microscope to ensure that growth is normal. Additional information may be recorded, such as drug insolubility or contamination, etc.

2. Add 10 μl of the fluorescent dye Resazurin to each well and incubate the plates for another 2 hours (until a color change is observed, but maximum 3 hours).

3. To determine an $IC_{50}$ value, the plate is read at excitation wavelength 530 nm and emission wavelength 590 nm (pre-set LILIT template file). Make sure that the values in each well are approximately 10 times the background values.

4. Data are transferred into a graphic program (Excel) and are evaluated to determine the $IC_{50}$ or analyzed using the fluorescent plate reader software (SoftMax).

TABLE 3

| In Vitro Screening Results | | | |
|---|---|---|---|
| Parasite | Strain | Stage | Reference Drug |
| T.b. rhodesiense | STIB 900 | trypomastigotes | melarsoprol |
| T. cruzi | Tulahuen C4 | amastigotes | benznidazole |
| L. donovani | MHOM-ET-67/L82 | amastigotes | Miltefosine |
| P. falciparum | K1 | IEF | chloroquine |
| Cytoxicity | L6 | — | podophyllotoxin |

| | $IC_{50}$ Values | | | | |
|---|---|---|---|---|---|
| ID | T.b. rhodensiense | T. cruzi | L. donovani | P. falciparum | Cytoxicity |
| melarsoprol | 0.003 | | | | |
| benznidazole | | 0.407 | | | |
| miltefosine | | | 0.178 | | |
| chloroquinine | | | | 0.059 | |

TABLE 3-continued

| podophyllotoxin | | | | | 0.007 |
|---|---|---|---|---|---|
| MEH-001 | >90 | >90 | >90 | >5 | >90 |
| MEH-001-B | 60.2 | >90 | >90 | >5 | >90 |
| MEH-002 | 10.3 | >90 | >90 | >5 | >90 |

All values as μg/mL
$^a$not soluble in DMSO
$^b$precipitates out in aqueous
Solvent: Water
MEH-001 is 2,2,2-trifluoro-ethylamino)-acetic acid.
MEH-001 B is [Carboxymethyl-(2,2,2-trifluoro-ethyl)-amino]-acetic acid.
MEH-002 is (3,3,3-trifluoro-propylamino)-acetic acid.

What is claimed is:

1. A phosphate isostere compound of formula Ia:

(Ia)

wherein:

A is independently selected from the group consisting of:
(a) an amino acid selected from the group consisting of tyrosine, serine, glycine and threonine;
(b) glucose or fructose;
(c) a substituted analogue of sphingosine;
(d) enol pyruvate or creatine;
(e) adenosine diphosphate or pyridoxal; and
(f) des-phosphonate glyphosate or des-phosphonate homo-glyphosate or other glyphosate analogues; and X is selected from the group consisting of:
(i) Oxygen;
(ii) Sulfur;
(iii) $CR_1R_2$ or $SiR_1R_2$, wherein $R_1$ and $R_2$ are each independently selected from the group consisting of hydrogen, alkyl, aryl, heteroaryl, halogen, hydroxyl, thiol, amino, ether, thioether, alkyl amine, dialkyl amine, aryl amine, diaryl amine, and alkyl aryl amine; or where X is $CR_1R_2$, $R_1$ and $R_2$ taken together form a cabonyl (=O), thiocarbonyl (=S) or substituted alkenyl (=C);
(iv) selenium or Se(O);
(v) $NR_3$, where $R_3$ is selected from the group consisting of hydrogen, alkyl, aryl, heteroaryl, heteroalicyclyl, hydroxyl, thiol, amino, ether, thioether, alkyl amine, dialkyl amine, aryl amine, diaryl amine, and alkyl aryl amine; and
(vi) a substituted or unsubstituted linker, 2-12 atoms in length, selected from the group consisting of substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, substituted or unsubstituted heteroalicyclyl, substituted or unsubstituted ether, substituted or unsubstituted thioether, and substituted or unsubstituted amine,
wherein when A is an amino acid then X is sulfur.

2. The compound of claim 1, wherein the compound is selected from the group consisting of formula Ic, Id, Ie, If, Ig, Ih, Ij, Ik, Ii, Il, and Io:

(Ic) 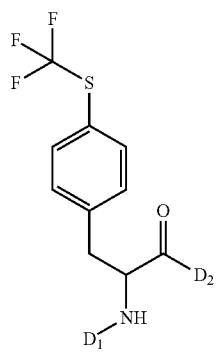

(Id) 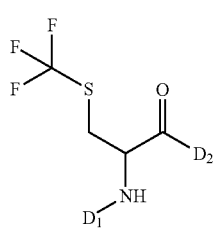

(Ie) 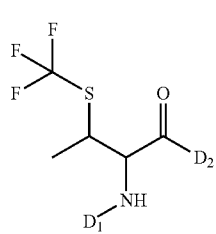

(If) 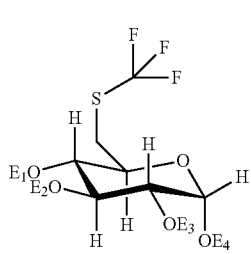

(Ig) 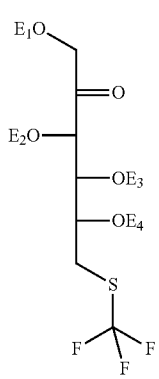

-continued (Ih) 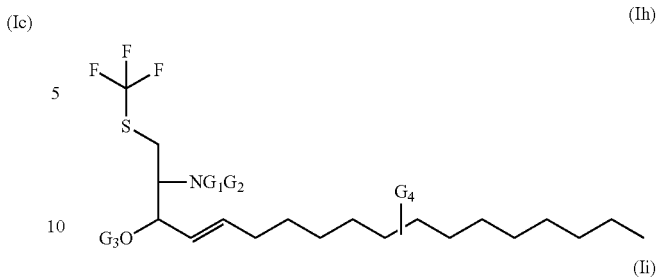

(Ii) 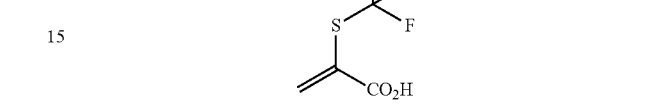

(Ij) 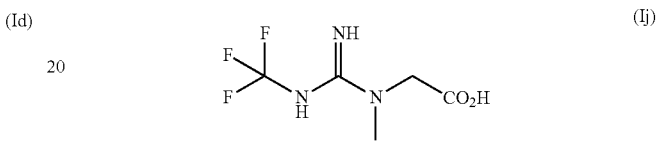

(Ik) 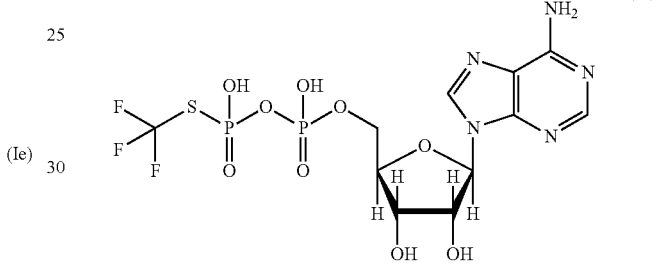

(Il) 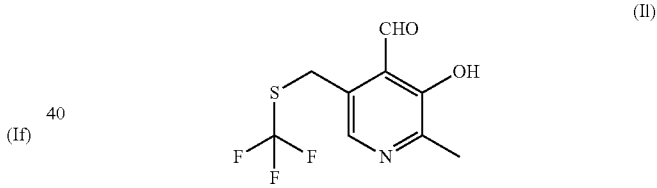

(Io) 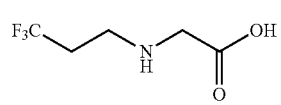

wherein:
$D_1$ and $D_2$ are each independently selected from the group consisting of hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, substituted or unsubstituted heteroalicyclyl, substituted or unsubstituted ether, substituted or unsubstituted thioether, and substituted or unsubstituted amine, or other independent amino acids or a sequence of one to one thousand (1-1000) of the amino acids;

$E_1$-$E_4$ are each independently selected from the group consisting of hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, substituted or unsubstituted heteroalicyclyl, substituted or unsubstituted ether, substituted or unsubstituted thioether, and substituted or unsubstituted amine or single carbohydrates or a combination of carbohydrates containing one to one thousand (1-1000) members; and
- $G_1$-$G_4$ are each independently selected from the group consisting of hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, substituted or unsubstituted heteroalicyclyl, substituted or unsubstituted ether, substituted or unsubstituted thioether, and substituted or unsubstituted amine or single carbohydrates or a combination of carbohydrates containing one to one thousand (1-1000) members.

3. A phosphate isostere compound selected from the group consisting of formula IIa, IIb, and IIc:

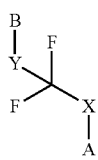

(IIa)

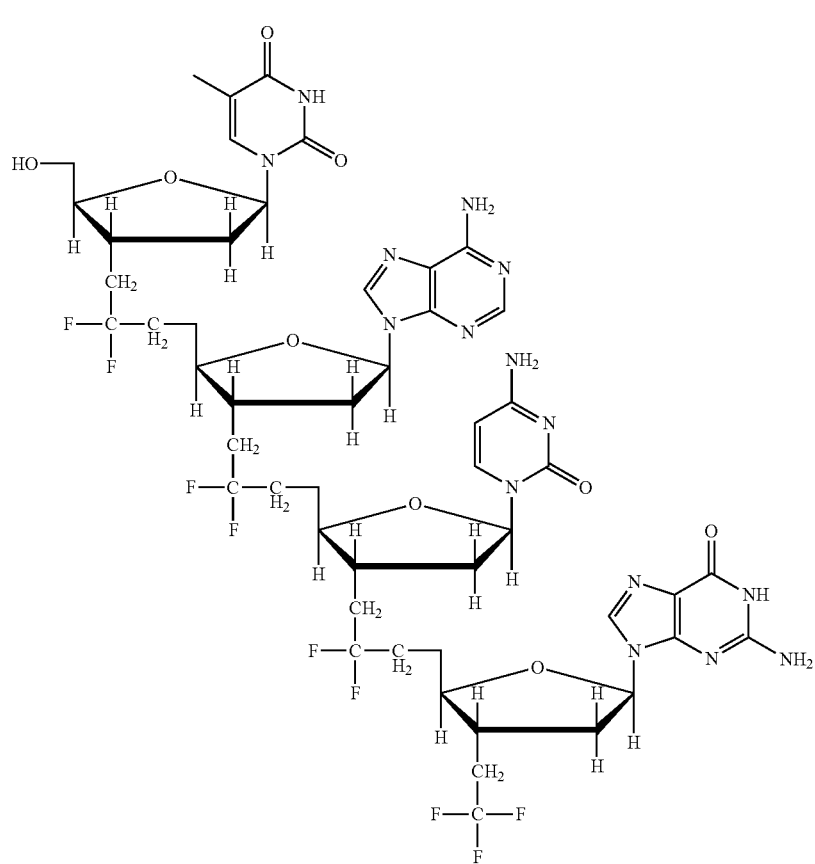

(IIb)

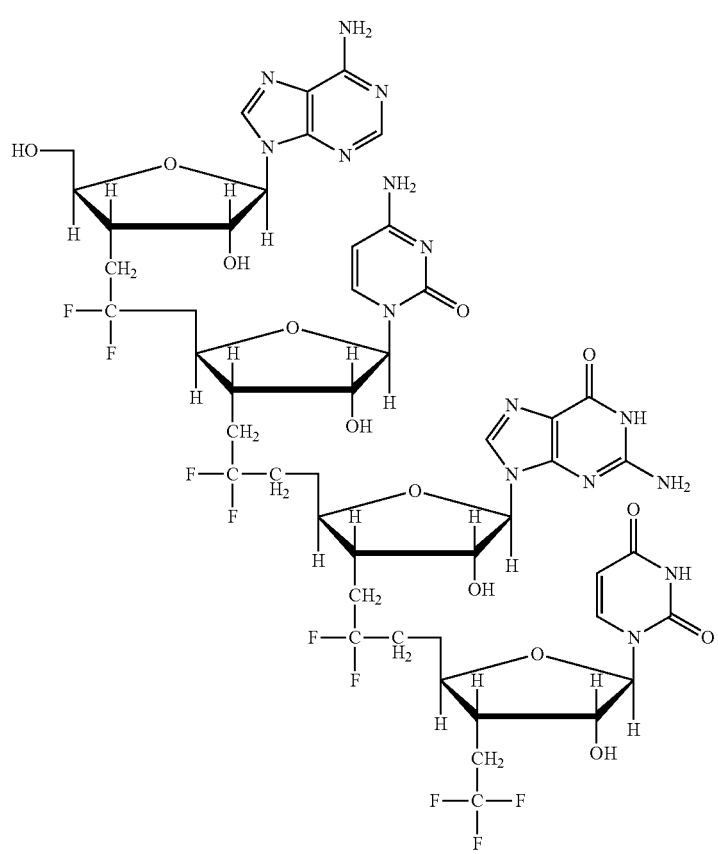

(IIc)

A and B are each independently des-phosphate nucleic acids; and

X and Y are each independently selected from the group consisting of:
(i) Oxygen;
(ii) Sulfur;
(iii) $CR_1R_2$ or $SiR_1R_2$, wherein $R_1$ and $R_2$ are each independently selected from the group consisting of hydrogen, alkyl, aryl, heteroaryl, halogen, hydroxyl, thiol, amino, ether, thioether, alkyl amine, dialkyl amine, aryl amine, diaryl amine, and alkyl aryl amine; or X is $CR_1R_2$, $R_1$ and $R_2$ taken together form a cabonyl (=O), thiocarbonyl (=S) or substituted alkenyl (=C);
(iv) selenium or Se(O);
(v) $NR_3$, where $R_3$ is selected from the group consisting of hydrogen, alkyl, aryl, heteroaryl, hydroxyl, thiol, amino, ether, thioether, alkyl amine, dialkyl amine, aryl amine, diaryl amine, and alkyl aryl amine; and
(vi) a substituted or unsubstituted linker, 2-12 atoms in length, selected from the group consisting of substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, substituted or unsubstituted heteroalicyclyl, substituted or unsubstituted ether, substituted or unsubstituted thioether, and substituted or unsubstituted amine.

4. A pharmaceutical composition comprising a therapeutically effective amount of a compound of claim 1 or claim 3 and a pharmaceutically acceptable carrier, excipient, or diluent.

5. A method of modulating an activity of a phosphoenolpyruvyl transferase (PEPT) enzyme, comprising: contacting the PEPT enzyme with a compound of claim 1, wherein the compound is a substrate of PEPT.

6. The method of claim 5, further comprising the step of detecting a change in the activity of the enzyme, and/or comparing the activity of the enzyme after the contacting to the activity of the enzyme before the contacting.

7. The method of claim 5, wherein the enzyme is contacted with the compound of claim 1 in vivo or in vitro.

8. The method of claim 5, wherein the compound of claim 1 selectively modulates the PEPT enzyme activity relative to other enzymes that utilize phosphoenolpyruvate as a substrate.

9. The method of claim 5, wherein the PEPT enzyme is selected from the group consisting of a bacterial PEPT enzyme, a fungal PEPT enzyme, a plant PEPT enzyme, a trypanosomal PEPT enzyme, a protozoan PEPT enzyme and any other non-mammalian PEPT enzyme.

* * * * *